US010240260B2

(12) United States Patent
Topolkaraev et al.

(10) Patent No.: US 10,240,260 B2
(45) Date of Patent: Mar. 26, 2019

(54) ABSORBENT ARTICLE CONTAINING A NONWOVEN WEB FORMED FROM A POROUS POLYOLEFIN FIBERS

(71) Applicant: Kimberly-Clark Worldwide, Inc., Neenah, WI (US)

(72) Inventors: Vasily A. Topolkaraev, Appleton, WI (US); Ryan J. McEneany, Appleton, WI (US); Antonio J. Carrillo, Appleton, WI (US); Mark M. Mleziva, Appleton, WI (US); Andy J. Meyer, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 517 days.

(21) Appl. No.: 14/895,237

(22) PCT Filed: Jun. 6, 2014

(86) PCT No.: PCT/IB2014/062022
§ 371 (c)(1),
(2) Date: Dec. 2, 2015

(87) PCT Pub. No.: WO2014/199272
PCT Pub. Date: Dec. 18, 2014

(65) Prior Publication Data
US 2016/0101208 A1  Apr. 14, 2016

Related U.S. Application Data

(60) Provisional application No. 61/833,981, filed on Jun. 12, 2013, provisional application No. 61/907,580, filed on Nov. 22, 2013.

(51) Int. Cl.
*A61F 13/15* (2006.01)
*D01F 6/06* (2006.01)
(Continued)

(52) U.S. Cl.
CPC ............... *D01F 6/06* (2013.01); *A61F 13/51* (2013.01); *A61L 15/225* (2013.01); *A61L 15/24* (2013.01);
(Continued)

(58) Field of Classification Search
CPC .. A61F 13/51; A61F 2013/51092; D01F 6/06; D01F 6/30; D01F 6/46; D01F 6/04;
(Continued)

(56) References Cited

U.S. PATENT DOCUMENTS 3,354,506 A   11/1967   Raley
3,423,255 A    1/1969   Joyce
(Continued)

FOREIGN PATENT DOCUMENTS

EP   0348887 A2   1/1990
EP   0348887 A3   1/1990
(Continued)

OTHER PUBLICATIONS

European Search Report dated Dec. 22, 2016, 3 pages.
(Continued)

*Primary Examiner* — Jacqueline Stephens
(74) *Attorney, Agent, or Firm* — Dority & Manning, P.A.

(57) ABSTRACT

An absorbent article containing a nonwoven web that includes a plurality of polyolefin fibers is provided. The polyolefin fibers are formed by a thermoplastic composition containing a continuous phase that includes a polyolefin matrix polymer and nanoinclusion additive is provided. The nanoinclusion additive is dispersed within the continuous phase as discrete nano-scale phase domains. When drawn, the nano-scale phase domains are able to interact with the matrix in a unique manner to create a network of nanopores.

29 Claims, 9 Drawing Sheets

(51) Int. Cl.

| | | |
|---|---|---|
| *D01D 5/247* | (2006.01) | |
| *D01F 6/46* | (2006.01) | |
| *A61F 13/51* | (2006.01) | |
| *A61L 15/22* | (2006.01) | |
| *A61L 15/24* | (2006.01) | |
| *A61L 15/42* | (2006.01) | |
| *B01J 20/26* | (2006.01) | |
| *B01J 20/28* | (2006.01) | |
| *B29C 47/00* | (2006.01) | |
| *B29C 47/88* | (2006.01) | |
| *C08J 9/00* | (2006.01) | |
| *D01F 6/30* | (2006.01) | |
| *B82Y 30/00* | (2011.01) | |
| *D01F 1/08* | (2006.01) | |
| *D01F 6/04* | (2006.01) | |
| *B29K 23/00* | (2006.01) | |

(52) U.S. Cl.
CPC ........... *A61L 15/425* (2013.01); *B01J 20/261* (2013.01); *B01J 20/28033* (2013.01); *B01J 20/28042* (2013.01); *B01J 20/28085* (2013.01); *B29C 47/0011* (2013.01); *B29C 47/0042* (2013.01); *B29C 47/0057* (2013.01); *B29C 47/8805* (2013.01); *C08J 9/0061* (2013.01); *D01D 5/247* (2013.01); *D01F 6/30* (2013.01); *D01F 6/46* (2013.01); *A61F 2013/51092* (2013.01); *B29K 2023/12* (2013.01); *B82Y 30/00* (2013.01); *C08J 2323/12* (2013.01); *C08J 2323/14* (2013.01); *D01F 1/08* (2013.01); *D01F 6/04* (2013.01)

(58) Field of Classification Search
CPC ...... A61L 15/225; A61L 15/24; A61L 15/425; B01J 20/28033; B01J 20/28042; B01J 20/28085; C08J 9/001; C08J 2323/12; C08J 2323/14; D01D 5/247; B82Y 30/00; B29C 47/0011; B29C 47/0042; B29C 47/0057; B29C 47/8805; B29K 2023/12
USPC .................................. 604/367, 366, 370, 372
See application file for complete search history.

(56) References Cited

U.S. PATENT DOCUMENTS

| | | |
|---|---|---|
| 3,650,649 A | 3/1972 | Schippers |
| 3,801,429 A | 4/1974 | Schrenk et al. |
| 3,802,817 A | 4/1974 | Matsuki et al. |
| 3,855,046 A | 12/1974 | Hansen et al. |
| 4,041,203 A | 8/1977 | Brock et al. |
| 4,100,324 A | 7/1978 | Anderson et al. |
| 4,282,735 A | 8/1981 | Break |
| 4,374,888 A | 2/1983 | Bornslaeger |
| 4,557,132 A | 12/1985 | Break |
| 4,698,372 A | 10/1987 | Moss |
| 4,704,116 A | 11/1987 | Enloe |
| 4,766,029 A | 8/1988 | Brock et al. |
| 4,797,468 A | 1/1989 | De Vries |
| 4,798,603 A | 1/1989 | Meyer et al. |
| 4,801,494 A | 1/1989 | Datta et al. |
| 4,908,026 A | 3/1990 | Sukiennik et al. |
| 4,937,299 A | 6/1990 | Ewen et al. |
| D315,990 S | 4/1991 | Blenke et al. |
| 5,169,706 A | 12/1992 | Collier, IV et al. |
| 5,179,164 A | 1/1993 | Lausberg et al. |
| 5,192,606 A | 3/1993 | Proxmire et al. |
| 5,213,881 A | 5/1993 | Timmons et al. |
| 5,218,071 A | 6/1993 | Tsutsui et al. |
| 5,248,309 A | 9/1993 | Serbiak et al. |
| 5,272,236 A | 12/1993 | Lai et al. |
| 5,278,272 A | 1/1994 | Lai et al. |
| 5,284,309 A | 2/1994 | Salvatore et al. |
| 5,284,703 A | 2/1994 | Everhart et al. |
| 5,322,728 A | 6/1994 | Davey et al. |
| 5,350,624 A | 9/1994 | Georger et al. |
| D358,035 S | 5/1995 | Zander et al. |
| 5,464,688 A | 11/1995 | Timmons et al. |
| 5,470,944 A | 11/1995 | Bonsignore |
| 5,472,775 A | 12/1995 | Obijeski et al. |
| 5,486,166 A | 1/1996 | Bishop et al. |
| 5,490,846 A | 2/1996 | Ellis et al. |
| 5,539,056 A | 7/1996 | Yang et al. |
| 5,571,619 A | 11/1996 | McAlpin et al. |
| 5,596,052 A | 1/1997 | Resconi et al. |
| 5,620,779 A | 4/1997 | Levy et al. |
| D384,508 S | 10/1997 | Zander et al. |
| D384,819 S | 10/1997 | Zander et al. |
| 5,702,377 A | 12/1997 | Collier, IV et al. |
| D390,708 S | 2/1998 | Brown |
| 5,766,760 A | 6/1998 | Tsai et al. |
| 5,770,682 A | 6/1998 | Ohara et al. |
| 5,821,327 A | 10/1998 | Oota et al. |
| 5,843,057 A | 12/1998 | McCormack |
| 5,855,999 A | 1/1999 | McCormack |
| 5,880,254 A | 3/1999 | Ohara et al. |
| 5,931,823 A | 8/1999 | Stokes et al. |
| 5,932,497 A | 8/1999 | Morman et al. |
| 5,962,112 A | 10/1999 | Haynes et al. |
| 5,968,643 A | 10/1999 | Topolkaraev et al. |
| 5,997,981 A | 12/1999 | McCormack et al. |
| 6,002,064 A | 12/1999 | Kobylivker et al. |
| D418,305 S | 1/2000 | Zander et al. |
| 6,015,764 A | 1/2000 | McCormack et al. |
| 6,037,033 A | 3/2000 | Hunter |
| 6,037,281 A | 3/2000 | Mathis et al. |
| 6,060,638 A | 5/2000 | Paul et al. |
| 6,071,451 A | 6/2000 | Wang et al. |
| D428,267 S | 7/2000 | Romano, III et al. |
| 6,090,325 A | 7/2000 | Wheat et al. |
| 6,093,665 A | 7/2000 | Sayovitz et al. |
| 6,096,014 A | 8/2000 | Haffner et al. |
| 6,111,163 A | 8/2000 | McCormack et al. |
| 6,150,002 A | 11/2000 | Varona |
| 6,214,933 B1 | 4/2001 | Wang et al. |
| 6,268,048 B1 | 7/2001 | Topolkaraev et al. |
| 6,326,458 B1 | 12/2001 | Gruber et al. |
| 6,380,445 B1 | 4/2002 | Rietz et al. |
| 6,389,864 B1 | 5/2002 | Chubb et al. |
| 6,461,457 B1 | 10/2002 | Taylor et al. |
| 6,485,446 B1 | 11/2002 | Brother et al. |
| 6,500,563 B1 | 12/2002 | Datta et al. |
| 6,582,810 B2 | 6/2003 | Heffelfinger |
| 6,586,073 B2 | 7/2003 | Perez et al. |
| 6,642,429 B1 | 11/2003 | Carter et al. |
| 6,663,611 B2 | 12/2003 | Blaney et al. |
| 6,716,203 B2 | 4/2004 | Sorebo et al. |
| 6,824,680 B2 | 11/2004 | Chandavasu et al. |
| 6,824,734 B2 | 11/2004 | Boggs et al. |
| 7,060,867 B2 | 6/2006 | Jameson |
| 7,097,904 B2 | 8/2006 | Ochi et al. |
| 7,141,168 B2 | 11/2006 | Sakamoto et al. |
| 7,341,776 B1 | 3/2008 | Milliren et al. |
| 7,984,591 B2 | 7/2011 | Cashin et al. |
| 7,998,579 B2 | 8/2011 | Lin et al. |
| 8,105,682 B2 | 1/2012 | Sun et al. |
| 8,268,738 B2 | 9/2012 | McEneany et al. |
| 8,313,818 B2 | 11/2012 | Vo et al. |
| 8,323,837 B2 | 12/2012 | Nishida et al. |
| 8,334,327 B2 | 12/2012 | Kaufman et al. |
| 8,362,145 B2 | 1/2013 | Li et al. |
| 8,603,614 B2 | 12/2013 | Lam et al. |
| 8,936,740 B2 | 1/2015 | Topolkaraev et al. |
| 2003/0116462 A1 | 6/2003 | Sorebo et al. |
| 2004/0002273 A1 | 1/2004 | Fitting et al. |
| 2005/0054255 A1 | 3/2005 | Morman et al. |
| 2005/0059941 A1 | 3/2005 | Baldwin et al. |
| 2005/0245162 A1 | 11/2005 | McCormack et al. |
| 2009/0318884 A1 | 12/2009 | Meyer et al. |
| 2010/0305529 A1 | 12/2010 | Ashton et al. |
| 2010/0313507 A1 | 12/2010 | Castro et al. |

(56) References Cited

U.S. PATENT DOCUMENTS

| | | | |
|---|---|---|---|
| 2011/0091714 A1 | 4/2011 | Chen et al. | |
| 2011/0183563 A1 | 7/2011 | Ochi et al. | |
| 2011/0252739 A1 | 10/2011 | Leeser et al. | |
| 2012/0040385 A1 | 2/2012 | Todolkaraev et al. | |
| 2012/0109090 A1 | 5/2012 | Reichardt et al. | |
| 2012/0164905 A1* | 6/2012 | Topolkaraev | D01F 8/14 442/364 |
| 2012/0225272 A1 | 9/2012 | Costeux et al. | |
| 2012/0231242 A1 | 9/2012 | Boyer et al. | |
| 2014/0011015 A1* | 1/2014 | Gardner | B29C 67/202 428/315.5 |

FOREIGN PATENT DOCUMENTS

| | | |
|---|---|---|
| EP | 0609881 A1 | 8/1994 |
| EP | 0609881 B1 | 8/1999 |
| EP | 1152025 A1 | 11/2001 |
| EP | 1152025 A4 | 11/2001 |
| WO | WO 99/32272 A1 | 7/1999 |
| WO | WO2009/152021 A2 | 12/2009 |
| WO | WO2009/152021 A3 | 12/2009 |
| WO | WO 2013/048675 | 4/2013 |
| WO | WO2014/199268 | 12/2014 |
| WO | WO2014/199269 | 12/2014 |
| WO | WO2014/199270 | 12/2014 |
| WO | WO2014/199271 | 12/2014 |
| WO | WO2014/199273 | 12/2014 |
| WO | WO2014/199274 | 12/2014 |
| WO | WO2014/199275 | 12/2014 |
| WO | WO2014/199276 | 12/2014 |
| WO | WO2014/199277 | 12/2014 |
| WO | WO2014/199278 | 12/2014 |
| WO | WO2014/199279 | 12/2014 |

OTHER PUBLICATIONS

Satoshi Nago et al., "Microporous Polypropylene Hollow Fibers Containing Poly(methylsilsesquioxane) Fillers", Journal of Applied Polymer Science, vol. 53, No. 12, Sep. 19, 1994, 9 pages.

Yukio Mizutani et al., "Microporous Polypropylene Fibers Containing Fine Particles of Poly(glycidylmethacrylate-co-divinylbenzene)", Journal of Applied Polymer Science, vol. 73, No. 8, Jun. 11, 1999, 5 pages.

Yukio Mizutani et al., "Microporous Polypropylene Fibers Containing Fine Particles of Poly(styrene-co-divinylbenzene) or Poly(glycidylmetharcrylate-co-divinylbenzene)", Journal of Applied Polymer Science, vol. 74, No. 3, Aug. 31, 1998, 6 pages.

Lee et al., "Development of Discrete Nanopores I: Tension of Polypropylene/Polyethylene Copolymer Blends," *Journal of Applied Polymer Science*, vol. 91, No. 6, Mar. 15, 2004, pp. 3462-3650.

International Search Report and Written Opinion for PCT/IB2014/062022 dated Sep. 16, 2014, 16 pages.

* cited by examiner

ABSORBENT ARTICLE CONTAINING A NONWOVEN WEB FORMED FROM A POROUS POLYOLEFIN FIBERS

RELATED APPLICATIONS

The present application is the national stage entry of International Patent Application No. PCT/IB2014/062022 having a filing date of Jun. 6, 2014, which claims priority to U.S. Provisional Application Ser. No. 61/833,981 (filed on Jun. 12, 2013) and 61/907,580 (filed on Nov. 22, 2013), which are incorporated herein by reference.

BACKGROUND OF THE INVENTION

Absorbent articles, such as diapers or feminine care articles, are generally constructed from an absorbent member that is positioned between a liquid-permeable topsheet, which defines a "body-facing" surface disposed toward the body, and a generally liquid-impermeable backsheet, which defines a "garment-facing" surface disposed away from the body. Polyolefin nonwoven webs are often used in the construction of components and/or layers of the absorbent article. For example, the backsheet of many absorbent articles is formed from polypropylene nonwoven webs. While having many beneficial properties, it remains desirable to reduce the carbon footprint of absorbent article products by minimizing the overall content of petroleum-based polyolefins. To this end, several attempts have been made to use gaseous blowing agents in the polyolefin fibers to create a cellular "foamed" structure, thereby lowering the density of the fibers and in turn, the polyolefin content. Unfortunately, the processability and tensile properties of the cellular structure is often compromised due to the uncontrolled pore size and distribution. As such, a need currently exists for fibers and webs of an absorbent article that can have a reduced consumption of petroleum-based polymers, but yet can also exhibit good properties.

SUMMARY OF THE INVENTION

In accordance with one embodiment of the present invention, an absorbent article is disclosed that contains an absorbent member positioned between a backsheet and topsheet. The absorbent article comprises a nonwoven web that includes a plurality of fibers formed from a thermoplastic composition that contains a continuous phase that includes a polyolefin matrix polymer and a nanoinclusion additive dispersed within the continuous phase in the form of discrete domains. The porous network is defined in the composition that includes a plurality of nanopores having an average cross-sectional dimension of about 800 nanometers or less.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which:

FIG. 9 is a schematic illustration of a process that may be used in one embodiment of the present invention to form polyolefin fibers;

DETAILED DESCRIPTION OF REPRESENTATIVE EMBODIMENTS

Figure 1:
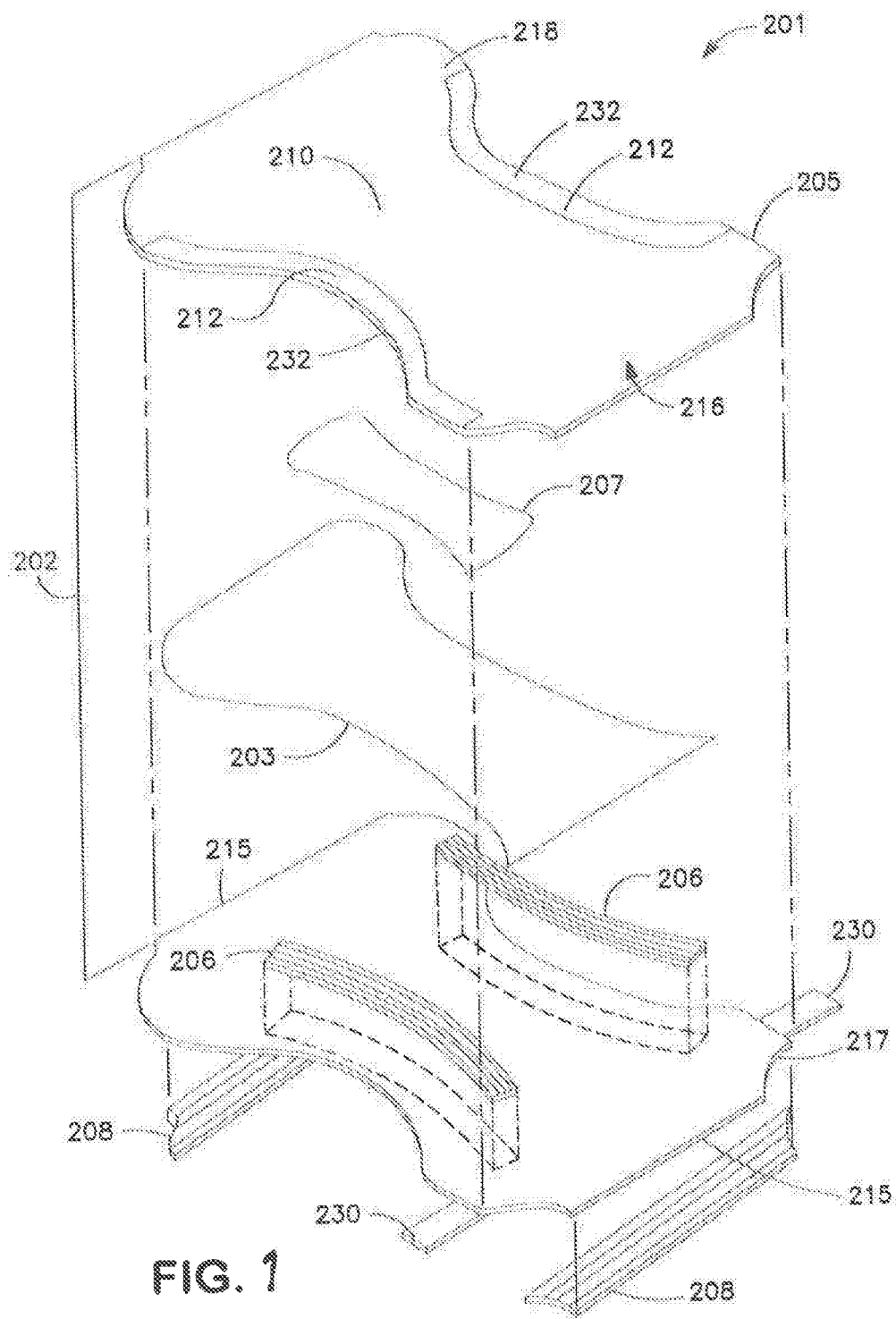
FIG. 1 is a perspective view of one embodiment of the absorbent article of the present invention.

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

Generally speaking, the present invention is directed to an absorbent article that is capable of absorbing water or other fluids. Examples of some absorbent articles include, but are not limited to, personal care absorbent articles, such as diapers, training pants, absorbent underpants, adult incontinence articles, feminine hygiene products (e.g., sanitary napkins), swim wear, baby wipes, mitt wipes, and so forth; medical absorbent articles, such as garments, fenestration materials, underpads, bandages, absorbent drapes, and medical wipes; food service wipers; clothing articles; and so forth. Regardless of the intended application, the absorbent article typically contains an absorbent member (e.g., core layer, surge layer, transfer delay layer, etc.) positioned between a backsheet and a topsheet. Notably, the absorbent member, backsheet, and/or topsheet, as well one or more other components of the absorbent article (e.g., ears, containment flaps, side panels, etc.) contain a nonwoven web that includes a plurality of fibers formed from a thermoplastic composition. The thermoplastic composition contains a continuous phase that includes a polyolefin matrix polymer, and also contains a nanoinclusion additive that is at least partially incompatible with the polyolefin matrix polymer so that it becomes dispersed within the continuous phase as discrete nano-scale phase domains. During drawing of the fiber, when the composition is subjected to a deformation and elongational strain, the present inventors have discovered that these nano-scale phase domains are able to interact in a unique manner to create a network of pores. Namely, it is believed that elongational strain can initiate intensive localized shear zones and/or stress intensity zones (e.g., normal stresses) near the discrete phase domains as a result of stress concentrations that arise from the incompatibility of the materials. These shear and/or stress intensity zones cause some initial debonding in the polyolefin matrix adjacent to the domains. Once initial pores are formed, the matrix located between domains can deform plastically to create internal stretched areas that locally narrow (or neck) and strain-harden. This process allows the formation of pores through the bulk of the composition that grow in the stretching direction, thereby leading to the formation of a porous network while the molecular orientation leads to strain-hardening that enhances mechanical strength.

Through the techniques noted above, a unique porous network may be formed in the polyolefin fiber so that the average percent volume occupied by the pores within a given unit volume of the fiber may be from about 15% to about 80% per cm³, in some embodiments from about 20% to about 70%, and in some embodiments, from about 30% to about 60% per cubic centimeter of the fiber. With such a pore volume, the composition may have a relatively low density, such as about 0.90 grams per cubic centimeter ("g/cm³") or less, in some embodiments about 0.85 g/cm³ or less, in some embodiments about 0.80 g/cm³ or less, in some embodiments from about 0.10 g/cm³ to about 0.75 g/cm³, and in some embodiments, from about 0.20 g/cm³ to about 0.70 g/cm³. A substantial portion of pores in the porous network are also of a "nano-scale" size ("nanopores"), such as those having an average cross-sectional dimension of about 800 nanometers or less, in some embodiments from about 5 to about 700 nanometers, and in some embodiments, from about 10 to about 500 nanometers. The term "cross-sectional dimension" generally refers to a characteristic dimension (e.g., width or diameter) of a pore, which is substantially orthogonal to its major axis (e.g., length) and also typically substantially orthogonal to the direction of the stress applied during drawing. The nanopores may also have an average axial dimension within the range of from about 100 to about 5000 nanometers, in some embodiments from about 50 to about 2000 nanometers, and in some embodiments, from about 100 to about 1000 nanometers. The "axial dimension" is the dimension in the direction of the major axis (e.g., length), which is typically in the direction of drawing. Such nanopores may, for example, constitute about 15 vol. % or more, in some embodiments about 20 vol. % or more, in some embodiments from about 30 vol. % to 100 vol. %, and in some embodiments, from about 40 vol. % to about 90 vol. % of the total pore volume in the polyolefin fiber.

Various embodiments of the present invention will now be described in more detail.

I. Thermoplastic Composition

A. Polyolefin Matrix

Polyolefins typically constitute from about 60 wt. % to about 99 wt. %, in some embodiments from about 60 wt. % to about 98 wt. %, and in some embodiments, from about 80 wt. % to about 95 wt. % of the thermoplastic composition. The polyolefin may have a melting temperature of from about 100° C. to about 220° C., in some embodiments from about 120° C. to about 200° C., and in some embodiments, from about 140° C. to about 180° C. The melting temperature may be determined using differential scanning calorimetry ("DSC") in accordance with ASTM D-3417. Suitable polyolefins may, for instance, include ethylene polymers (e.g., low density polyethylene ("LDPE"), high density polyethylene ("HDPE"), linear low density polyethylene ("LLDPE"), etc.), propylene homopolymers (e.g., syndiotactic, atactic, isotactic, etc.), propylene copolymers, and so forth. In one particular embodiment, the polymer is a propylene polymer, such as homopolypropylene or a copolymer of propylene. The propylene polymer may, for instance, be formed from a substantially isotactic polypropylene homopolymer or a copolymer containing equal to or less than about 10 wt. % of other monomers, i.e., at least about 90% by weight propylene. Such homopolymers may have a melting point of from about 140° C. to about 170° C.

Of course, other polyolefins may also be employed in the composition of the present invention. In one embodiment, for example, the polyolefin may be a copolymer of ethylene or propylene with another α-olefin, such as a $C_3$-$C_{20}$ α-olefin or $C_3$-$C_{12}$ α-olefin. Specific examples of suitable α-olefins include 1-butene; 3-methyl-1-butene; 3,3-dimethyl-1-butene; 1-pentene; 1-pentene with one or more methyl, ethyl or propyl substituents; 1-hexene with one or more methyl, ethyl or propyl substituents; 1-heptene with one or more methyl, ethyl or propyl substituents; 1-octene with one or more methyl, ethyl or propyl substituents; 1-nonene with one or more methyl, ethyl or propyl substituents; ethyl, methyl or dimethyl-substituted 1-decene; 1-dodecene; and styrene. Particularly desired α-olefin comonomers are 1-butene, 1-hexene and 1-octene. The ethylene or propylene content of such copolymers may be from about 60 mole % to about 99 mole %, in some embodiments from about 80 mole % to about 98.5 mole %, and in some embodiments, from about 87 mole % to about 97.5 mole %. The α-olefin content may likewise range from about 1 mole % to about 40 mole %, in some embodiments from about 1.5 mole % to about 15 mole %, and in some embodiments, from about 2.5 mole % to about 13 mole %.

Exemplary olefin copolymers for use in the present invention include ethylene-based copolymers available under the designation EXACT™ from ExxonMobil Chemical Company of Houston, Tex. Other suitable ethylene copolymers are available under the designation ENGAGE™, AFFINITY™, DOWLEX™ (LLDPE) and ATTANE™ (ULDPE) from Dow Chemical Company of Midland, Mich. Other suitable ethylene polymers are described in U.S. Pat. No. 4,937,299 to Ewen et al.; U.S. Pat. No. 5,218,071 to Tsutsui et al.; U.S. Pat. No. 5,272,236 to Lai, et al.; and U.S. Pat. No. 5,278,272 to Lai, et al. Suitable propylene copolymers are also commercially available under the designations VISTAMAXX™ from ExxonMobil Chemical Co. of Houston, Tex.; FINA™ (e.g., 8573) from Atofina Chemicals of Feluy, Belgium; TAFMER™ available from Mitsui Petrochemical Industries; and VERSIFY™ available from Dow Chemical Co. of Midland, Mich. Suitable polypropylene homopolymers may include Exxon Mobil 3155 polypropylene, Exxon Mobil Achieve™ resins, and Total M3661 PP resin. Other examples of suitable propylene polymers are described in U.S. Pat. No. 6,500,563 to Datta, et al.; U.S. Pat. No. 5,539,056 to Yang, et al.; and U.S. Pat. No. 5,596,052 to Resconi, et al.

Any of a variety of known techniques may generally be employed to form the olefin copolymers. For instance, olefin polymers may be formed using a free radical or a coordination catalyst (e.g., Ziegler-Natta). Preferably, the olefin polymer is formed from a single-site coordination catalyst, such as a metallocene catalyst. Such a catalyst system produces ethylene copolymers in which the comonomer is randomly distributed within a molecular chain and uniformly distributed across the different molecular weight fractions. Metallocene-catalyzed polyolefins are described, for instance, in U.S. Pat. No. 5,571,619 to McAlpin et al.; U.S. Pat. No. 5,322,728 to Davis et al.; U.S. Pat. No. 5,472,775 to Obijeski et al.; U.S. Pat. No. 5,272,236 to Lai et al.; and U.S. Pat. No. 6,090,325 to Wheat, et al. Examples of metallocene catalysts include bis(n-butylcyclopentadienyl)titanium dichloride, bis(n-butylcyclopentadienyl)zirconium dichloride, bis(cyclopentadienyl)scandium chloride, bis(indenyl)zirconium dichloride, bis(methylcyclopentadienyl)titanium dichloride, bis(methylcyclopentadienyl)zirconium dichloride, cobaltocene, cyclopentadienyttitanium trichloride, ferrocene, hafnocene dichloride, isopropyl(cyclopentadienyl,-1-flourenyl)zirconium dichloride, molybdocene dichloride, nickelocene, niobocene dichloride, ruthenocene, titanocene dichloride, zirconocene chloride hydride, zirconocene dichloride, and so forth. Polymers made using metallocene catalysts typically have a narrow molecular weight range. For instance, metallocene-catalyzed polymers may have polydispersity numbers ($M_w/M_n$) of below 4, controlled short chain branching distribution, and controlled isotacticity.

B. Nanoinclusion Additive

As used herein, the term "nanoinclusion additive" generally refers to a material that is capable of being dispersed within the polymer matrix in the form of discrete domains of a nano-scale size. For example, prior to drawing, the domains may have an average cross-sectional dimension of from about 1 to about 1000 nanometers, in some embodiments from about 5 to about 800 nanometers, in some embodiments from about 10 to about 500 nanometers, and in some embodiments from about 20 to about 200 nanometers. The domains may have a variety of different shapes, such as elliptical, spherical, cylindrical, plate-like, tubular, etc. In one embodiment, for example, the domains have a substantially elliptical shape. The nanoinclusion additive is typically employed in an amount of from about 0.05 wt. % to about 20 wt. %, in some embodiments from about 0.1 wt. % to about 10 wt. %, and in some embodiments, from about 0.5 wt. % to about 5 wt. % of the thermoplastic composition, based on the weight of the continuous phase polyolefin matrix. The concentration of the nanoinclusion additive in the entire thermoplastic composition may likewise be from about 0.01 wt. % to about 15 wt. %, in some embodiments from about 0.05 wt. % to about 10 wt. %, and in some embodiments, from about 0.3 wt. % to about 6 wt. % of the thermoplastic composition.

The nanoinclusion additive is partially incompatible with the polyolefin in the sense that it can be substantially uniformly distributed within the polyolefin matrix, but in the form of discrete domains. Such partial incompatibility can be accomplished in a variety of ways. In certain embodiments, for example, the nanoinclusion additive may possess a nonpolar component (e.g., olefin) that is compatible with the polyolefin matrix and allows it to become uniformly distributed therein. Nevertheless, the additive may also include a polar component that is incompatible with the polyolefin matrix, thereby allowing it to coalesce or segregate into discrete domains. Such a component may include low or high molecular weight polar molecular segments or blocks, ionic groups, charged or uncharged polar domains, and/or polar molecular groups. Alternatively, the additive may be entirely nonpolar in nature, but possess certain physical properties that still allow for discrete domains to be formed. For example, in certain embodiments, the nanoinclusion additive may be compatible or miscible with the polyolefin above a certain temperature, but phase separate at temperatures lower than the critical solution temperature. In this manner, the nanoinclusion additive can form a stable blend with the polyolefin in the melt phase, but as the temperature decreases, the continuous phase crystallizes and segregates so that the nanoinclusion additive can phase separate, coalesce, and form separate nano-scale domains.

The particular state or form of the nanoinclusion additive is not critical so long as the desired domains can be formed. For example, in some embodiments, the nanoinclusion additive can be in the form of a liquid or semi-solid at room temperature (e.g., 25° C.). Such a liquid can be readily dispersed in the matrix to form a metastable dispersion, and then quenched to preserve the domain size by reducing the temperature of the blend. The kinematic viscosity of such a liquid or semi-solid material is typically from about 0.7 to about 200 centistokes ("cs"), in some embodiments from about 1 to about 100 cs, and in some embodiments, from about 1.5 to about 80 cs, determined at 40° C. Suitable liquids or semi-solids may include, for instance, silicones, silicone-polyether copolymers, aliphatic polyesters, aromatic polyesters, alkylene glycols (e.g., ethylene glycol, diethylene glycol, triethylene glycol, tetraethylene glycol, propylene glycol, polyethylene glycol, polypropylene glycol, polybutylene glycol, etc.), alkane diols (e.g., 1,3-propanediol, 2,2-dimethyl-1,3-propanediol, 1,3-butanediol, 1,4-butanediol, 1,5-pentanediol, 1,6-hexanediol, 2,2,4-trimethyl-1,6 hexanediol, 1,3-cyclohexanedimethanol, 1,4-cyclohexanedimethanol, 2,2,4,4-tetramethyl-1,3-cyclobutanediol, etc.), amine oxides (e.g., octyldimethylamine oxide), fatty acid esters, fatty acid amides (e.g., oleamide, erucamide, stearamide, ethylene bis(stearamide), etc.), mineral, and vegetable oils, and so forth. One particularly suitable liquid or semi-solid is polyether polyol, such as commercially available under the trade name Pluriol® WI from BASF Corp.

In yet other embodiments, the nanoinclusion additive is in the form of a solid, which may be amorphous, crystalline, or semi-crystalline. For example, the nanoinclusion additive may be polymeric in nature and possess a relatively high molecular weight to help improve the melt strength and stability of the thermoplastic composition. As indicated above, the nanoinclusion additive is partially incompatible with the polyolefin matrix. One example of such an additive is a microcrystalline polyolefin wax, which is typically derived from ethylene and/or $C_3$-$C_{10}$-alk-1-enes, such as from propylene, 1-butene, 1-pentene, 1-hexene, 1-heptene, 1-octene, 1-nonene, and 1-decene. Microcrystalline waxes typically have a relatively low melting temperature, such as from about 30° C. to about 150° C., in some embodiments from about 50° C. to about 140° C., and in some embodiments, from about 80° C. to about 130° C. At such low melting temperatures, the wax can form a miscible blend with the polyolefin when in the melt phase, but as the temperature decreases and polymer crystallizes or solidifies, the wax will segregate and coalesce forming separate nano-scale domains.

Another example of a polymeric nanoinclusion additive is a functionalized polyolefin that contains a polar and nonpolar component. The polar component may, for example, be provided by one or more functional groups and the nonpolar component may be provided by an olefin. The olefin component of the nanoinclusion additive may generally be formed from any linear or branched α-olefin monomer, oligomer, or polymer (including copolymers) derived from an olefin monomer, such as described above. The functional group of the nanoinclusion additive may be any group, molecular segment and/or block that provides a polar component to the molecule and is not compatible with the polyolefin matrix polymer. Examples of molecular segment and/or blocks not compatible with polyolefin may include acrylates, styrenics, polyesters, polyamides, etc. The functional group can have an ionic nature and comprise charged metal ions. Particularly suitable functional groups are maleic anhydride, maleic acid, fumaric acid, maleimide, maleic acid hydrazide, a reaction product of maleic anhydride and diamine, methylnadic anhydride, dichloromaleic anhydride, maleic acid amide, etc. Maleic anhydride modified polyolefins are particularly suitable for use in the present invention. Such modified polyolefins are typically formed by grafting maleic anhydride onto a polymeric backbone material. Such maleated polyolefins are available from E. I. du Pont de Nemours and Company under the designation Fusabond®, such as the P Series (chemically modified polypropylene), E Series (chemically modified polyethylene), C Series (chemically modified ethylene vinyl acetate), A Series (chemically modified ethylene acrylate copolymers or terpolymers), or N Series (chemically modified ethylene-propylene, ethylene-propylene diene monomer ("EPDM") or ethylene-octene). Alternatively, maleated polyolefins are also available from Chemtura Corp. under the designation Polybond®, Eastman Chemical Company under the designation Eastman G series, and Arkema under the designation Orevac®.

In certain embodiments, the polymeric nanoinclusion additive may also be reactive. One example of such a reactive nanoinclusion additive is a polyepoxide that contains, on average, at least two oxirane rings per molecule. Without intending to be limited by theory, it is believed that such polyepoxide molecules can undergo a reaction (e.g., chain extension, side chain branching, grafting, copolymer formation, etc.) with certain components of the composition to improve melt strength without significantly reducing glass transition temperature. The reactive additive can also provide compatibilization between the polyolefin and other more polar additives, such as microinclusion additives, and can improve the uniformity of dispersion and reduce the size of microinclusion additives. For example, as will be described in more detail below, certain embodiments of the present invention may employ a polyester as a microinclusion additive. In such embodiments, the reactive nanoinclusion additive may enable a nucleophilic ring-opening reaction via a carboxyl terminal group of the polyester (esterification) or via a hydroxyl group (etherification). Oxazoline side reactions may likewise occur to form ester-amide moieties. Through such reactions, the molecular weight of a polyester microinclusion additive may be increased to counteract the degradation often observed during melt processing. The present inventors have discovered that too much of a reaction can lead to crosslinking between polymer backbones. If such crosslinking is allowed to proceed to a significant extent, the resulting polymer blend can become brittle and difficult to process into a fiber with the desired strength and elongation properties.

In this regard, the present inventors have discovered that polyepoxides having a relatively low epoxy functionality may be particularly effective, which may be quantified by its "epoxy equivalent weight." The epoxy equivalent weight reflects the amount of resin that contains one molecule of an epoxy group, and it may be calculated by dividing the number average molecular weight of the modifier by the number of epoxy groups in the molecule. The polyepoxide of the present invention typically has a number average molecular weight from about 7,500 to about 250,000 grams per mole, in some embodiments from about 15,000 to about 150,000 grams per mole, and in some embodiments, from about 20,000 to 100,000 grams per mole, with a polydispersity index typically ranging from 2.5 to 7. The polyepoxide may contain less than 50, in some embodiments from 5 to 45, and in some embodiments, from 15 to 40 epoxy groups. In turn, the epoxy equivalent weight may be less than about 15,000 grams per mole, in some embodiments from about 200 to about 10,000 grams per mole, and in some embodiments, from about 500 to about 7,000 grams per mole.

The polyepoxide may be a linear or branched, homopolymer or copolymer (e.g., random, graft, block, etc.) containing terminal epoxy groups, skeletal oxirane units, and/or pendent epoxy groups. The monomers employed to form such polyepoxides may vary. In one particular embodiment, for example, the polyepoxide contains at least one epoxy-functional (meth)acrylic monomeric component. As used herein, the term "(meth)acrylic" includes acrylic and methacrylic monomers, as well as salts or esters thereof, such as acrylate and methacrylate monomers. For example, suitable epoxy-functional (meth)acrylic monomers may include, but are not limited to, those containing 1,2-epoxy groups, such as glycidyl acrylate and glycidyl methacrylate. Other suitable epoxy-functional monomers include allyl glycidyl ether, glycidyl ethacrylate, and glycidyl itoconate.

The polyepoxide typically has a relatively high molecular weight, as indicated above, so that it may not only result in chain extension, but also help to achieve the desired blend morphology. The resulting melt flow rate of the polymer is thus typically within a range of from about 10 to about 200 grams per 10 minutes, in some embodiments from about 40 to about 150 grams per 10 minutes, and in some embodiments, from about 60 to about 120 grams per 10 minutes, determined at a load of 2160 grams and at a temperature of 190° C.

The polyepoxide also typically includes at least one linear or branched α-olefin monomer, such as those having from 2 to 20 carbon atoms and preferably from 2 to 8 carbon atoms. Specific examples include ethylene, propylene, 1-butene; 3-methyl-1-butene; 3,3-dimethyl-1-butene; 1-pentene; 1-pentene with one or more methyl, ethyl or propyl substituents; 1-hexene with one or more methyl, ethyl or propyl substituents; 1-heptene with one or more methyl, ethyl or propyl substituents; 1-octene with one or more methyl, ethyl or propyl substituents; 1-nonene with one or more methyl, ethyl or propyl substituents; ethyl, methyl or dimethyl-substituted 1-decene; 1-dodecene; and styrene. Particularly desired α-olefin comonomers are ethylene and propylene. Another suitable monomer may include a (meth)acrylic monomer that is not epoxy-functional. Examples of such (meth)acrylic monomers may include methyl acrylate, ethyl acrylate, n-propyl acrylate, i-propyl acrylate, n-butyl acrylate, s-butyl acrylate, i-butyl acrylate, t-butyl acrylate, n-amyl acrylate, i-amyl acrylate, isobornyl acrylate, n-hexyl acrylate, 2-ethylbutyl acrylate, 2-ethylhexyl acrylate, n-octyl acrylate, n-decyl acrylate, methylcyclohexyl acrylate, cyclopentyl acrylate, cyclohexyl acrylate, methyl methacrylate, ethyl methacrylate, 2-hydroxyethyl methacrylate, n-propyl methacrylate, n-butyl methacrylate, i-propyl methacrylate, i-butyl methacrylate, n-amyl methacrylate, n-hexyl methacrylate, i-amyl methacrylate, s-butyl-methacrylate, t-butyl methacrylate, 2-ethylbutyl methacrylate, methylcyclohexyl methacrylate, cinnamyl methacrylate, crotyl methacrylate, cyclohexyl methacrylate, cyclopentyl methacrylate, 2-ethoxyethyl methacrylate, isobornyl methacrylate, etc., as well as combinations thereof.

In one particularly desirable embodiment of the present invention, the polyepoxide is a terpolymer formed from an epoxy-functional (meth)acrylic monomeric component, α-olefin monomeric component, and non-epoxy functional (meth)acrylic monomeric component. For example, the polyepoxide may be poly(ethylene-co-methylacrylate-co-glycidyl methacrylate), which has the following structure:

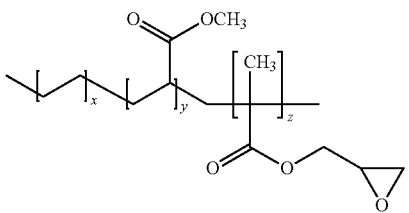

wherein, x, y, and z are 1 or greater.

The epoxy functional monomer may be formed into a polymer using a variety of known techniques. For example, a monomer containing polar functional groups may be grafted onto a polymer backbone to form a graft copolymer. Such grafting techniques are well known in the art and described, for instance, in U.S. Pat. No. 5,179,164. In other embodiments, a monomer containing epoxy functional groups may be copolymerized with a monomer to form a block or random copolymer using known free radical polymerization techniques, such as high pressure reactions, Ziegler-Natta catalyst reaction systems, single site catalyst (e.g., metallocene) reaction systems, etc.

The relative portion of the monomeric component(s) may be selected to achieve a balance between epoxy-reactivity and melt flow rate. More particularly, high epoxy monomer contents can result in good reactivity, but too high of a content may reduce the melt flow rate to such an extent that the polyepoxide adversely impacts the melt strength of the polymer blend. Thus, in most embodiments, the epoxy-functional (meth)acrylic monomer(s) constitute from about 1 wt. % to about 25 wt. %, in some embodiments from about 2 wt. % to about 20 wt. %, and in some embodiments, from about 4 wt. % to about 15 wt. % of the copolymer. The α-olefin monomer(s) may likewise constitute from about 55 wt. % to about 95 wt. %, in some embodiments from about 60 wt. % to about 90 wt. %, and in some embodiments, from about 65 wt. % to about 85 wt. % of the copolymer. When employed, other monomeric components (e.g., non-epoxy functional (meth)acrylic monomers) may constitute from about 5 wt. % to about 35 wt. %, in some embodiments from about 8 wt. % to about 30 wt. %, and in some embodiments, from about 10 wt. % to about 25 wt. % of the copolymer. One specific example of a suitable polyepoxide that may be used in the present invention is commercially available from Arkema under the name LOTADER® AX8950 or AX8900. LOTADER® AX8950, for instance, has a melt flow rate of 70 to 100 g/10 min and has a glycidyl methacrylate monomer content of 7 wt. % to 11 wt. %, a methyl acrylate monomer content of 13 wt. % to 17 wt. %, and an ethylene monomer content of 72 wt. % to 80 wt. %. Another suitable polyepoxide is commercially available from DuPont under the name ELVALOY® PTW, which is a terpolymer of ethylene, butyl acrylate, and glycidyl methacrylate and has a melt flow rate of 12 g/10 min.

In addition to controlling the type and relative content of the monomers used to form the polyepoxide, the overall weight percentage may also be controlled to achieve the desired benefits. For example, if the modification level is too low, the desired increase in melt strength and mechanical properties may not be achieved. The present inventors have also discovered, however, that if the modification level is too high, processing may be restricted due to strong molecular interactions (e.g., crosslinking) and physical network formation by the epoxy functional groups. Thus, the polyepoxide is typically employed in an amount of from about 0.05 wt. % to about 10 wt. %, in some embodiments from about 0.1 wt. % to about 8 wt. %, in some embodiments from about 0.5 wt. % to about 5 wt. %, and in some embodiments, from about 1 wt. % to about 3 wt. %, based on the weight of the polyolefins employed in the composition. The polyepoxide may also constitute from about 0.05 wt. % to about 10 wt. %, in some embodiments from about 0.05 wt. % to about 8 wt. %, in some embodiments from about 0.1 wt. % to about 5 wt. %, and in some embodiments, from about 0.5 wt. % to about 3 wt. %, based on the total weight of the composition.

Other reactive nanoinclusion additives may also be employed in the present invention, such as oxazoline-functionalized polymers, cyanide-functionalized polymers, etc. When employed, such reactive nanoinclusion additives may be employed within the concentrations noted above for the polyepoxide. In one particular embodiment, an oxazoline-grafted polyolefin may be employed that is a polyolefin grafted with an oxazoline ring-containing monomer. The oxazoline may include a 2-oxazoline, such as 2-vinyl-2-oxazoline (e.g., 2-isopropenyl-2-oxazoline), 2-fatty-alkyl-2-oxazoline (e.g., obtainable from the ethanolamide of oleic acid, linoleic acid, palmitoleic acid, gadoleic acid, erucic acid and/or arachidonic acid) and combinations thereof. In another embodiment, the oxazoline may be selected from ricinoloxazoline maleinate, undecyl-2-oxazoline, soya-2-oxazoline, ricinus-2-oxazoline and combinations thereof, for example. In yet another embodiment, the oxazoline is selected from 2-isopropenyl-2-oxazoline, 2-isopropenyl-4,4-dimethyl-2-oxazoline and combinations thereof.

In certain embodiments of the present invention, multiple nanoinclusion additives may be employed in combination. For instance, a first nanoinclusion additive (e.g., polyepoxide) may be dispersed in the form of domains having an average cross-sectional dimension of from about 50 to about 500 nanometers, in some embodiments from about 60 to about 400 nanometers, and in some embodiments from about 80 to about 300 nanometers. A second nanoinclusion additive may also be dispersed in the form of domains that are smaller than the first nanoinclusive additive, such as those having an average cross-sectional dimension of from about 1 to about 50 nanometers, in some embodiments from about 2 to about 45 nanometers, and in some embodiments from about 5 to about 40 nanometers. When employed, the first and/or second nanoinclusion additives typically constitute from about 0.05 wt. % to about 20 wt. %, in some embodiments from about 0.1 wt. % to about 10 wt. %, and in some embodiments, from about 0.5 wt. % to about 5 wt. % of the thermoplastic composition, based on the weight of the continuous phase (matrix polymer(s)). The concentration of the first and/or second nanonclusion additives in the entire thermoplastic composition may likewise be from about 0.01 wt. % to about 15 wt. %, in some embodiments from about 0.05 wt. % to about 10 wt. %, and in some embodiments, from about 0.1 wt. % to about 8 wt. % of the thermoplastic composition.

Nanofillers may optionally be employed for the second nanoinclusion additive, examples of which may include carbon black, carbon nanotubes, carbon nanofibers, nanoclays, metal nanoparticles, nanosilica, nanoalumina, etc. Nanoclays are particularly suitable. The term "nanoclay" generally refers to nanoparticles of a clay material (a naturally occurring mineral, an organically modified mineral, or a synthetic nanomaterial), which typically have a platelet structure. Examples of nanoclays include, for instance, montmorillonite (2:1 layered smectite clay structure), bentonite (aluminium phyllosilicate formed primarily of montmorillonite), kaolinite (1:1 aluminosilicate having a platy structure and empirical formula of $Al_2Si_2O_5(OH)_4$), halloysite (1:1 aluminosilicate having a tubular structure and empirical formula of $Al_2Si_2O_5(OH)_4$), etc. An example of a suitable nanoclay is Cloisite®, which is a montmorillonite nanoclay and commercially available from Southern Clay Products, Inc. Other examples of synthethic nanoclays include but are not limited to a mixed-metal hydroxide nanoclay, layered double hydroxide nanoclay (e.g., sepiocite), laponite, hectorite, saponite, indonite, etc.

If desired, the nanoclay may contain a surface treatment to help improve compatibility with the matrix polymer (e.g., polyester). The surface treatment may be organic or inorganic. In one embodiment, an organic surface treatment is employed that is obtained by reacting an organic cation with the clay. Suitable organic cations may include, for instance, organoquaternary ammonium compounds that are capable of exchanging cations with the clay, such as dimethyl bis[hydrogenated tallow]ammonium chloride (2M2HT), methyl benzyl bis[hydrogenated tallow]ammonium chloride (MB2HT), methyl tris[hydrogenated tallow alkyl]chloride (M3HT), etc. Examples of commercially available organic nanoclays may include, for instance, Dellite® 43B (Laviosa Chimica of Livorno, Italy), which is a montmorillonite clay modified with dimethyl benzylhydrogenated tallow ammonium salt. Other examples include Cloisite® 25A and Cloisite® 30B (Southern Clay Products) and Nanofil 919 (Süd Chemie). If desired, the nanofiller can be blended with a carrier resin to form a masterbatch that enhances the compatibility of the additive with the other polymers in the composition. Particularly suitable carrier resins include, for instance, polyesters (e.g., polylactic acid, polyethylene terephthalate, etc.); polyolefins (e.g., ethylene polymers, propylene polymers, etc.); and so forth, as described in more detail above.

Regardless of the material employed, the nanoinclusion additive is typically selected to have a certain viscosity (or melt flow rate) to ensure that the discrete domains and resulting pores can be adequately maintained. For example, if the viscosity of the nanoinclusion additive is too low (or melt flow rate is too high), it tends to flow and disperse uncontrollably through the continuous phase. This results in lamellar, plate-like domains or co-continuous phase structures that are difficult to maintain and also likely to prematurely fracture. Conversely, if the viscosity is too high (or melt flow rate is too low), it tends to clump together and form very large elliptical domains, which are difficult to disperse during blending. This may cause uneven distribution of the nanoinclusion additive through the entirety of the continuous phase. For instance, the ratio of the melt flow rate of the polyolefin to the melt flow rate of a polymeric nanoinclusion additive, for instance, may be from about 0.2 to about 8, in some embodiments from about 0.5 to about 6, and in some embodiments, from about 1 to about 5. The nanoinclusion additive may, for example, have a melt flow rate (on a dry basis) of from about 0.1 to about 100 grams per 10 minutes, in some embodiments from about 0.5 to about 50 grams per 10 minutes, and in some embodiments, from about 5 to about 15 grams per 10 minutes, determined at a load of 2160 grams and at a temperature at least about 40° C. above the melting temperature (e.g., at 190° C.) in accordance with ASTM D1238. The polyolefin may likewise have a melt flow rate (on a dry basis) of from about 0.5 to about 80 grams per 10 minutes, in some embodiments from about 1 to about 40 grams per 10 minutes, and in some embodiments, from about 5 to about 20 grams per 10 minutes, determined at a load of 2160 grams and at a temperature at least about 40° C. above the melting temperature (e.g., at 230° C.) in accordance with ASTM D1238.

C. Microinclusion Additive

Although not required, the composition of the present invention may also employ a microinclusion additive. As used herein, the term "microinclusion additive" generally refers to any material that is capable of being dispersed within the polymer matrix in the form of discrete domains of a micro-scale size. For example, prior to drawing, the domains may have an average cross-sectional dimension of from about 0.1 μm to about 25 μm, in some embodiments from about 0.5 μm to about 20 μm, and in some embodiments from about 1 μm to about 10 μm. When employed, the present inventors have discovered that the micro-scale and nano-scale phase domains are able to interact in a unique manner when subjected to a deformation and elongational strain (e.g., drawing) to create a network of pores. Namely, it is believed that elongational strain can initiate intensive localized shear zones and/or stress intensity zones (e.g., normal stresses) near the micro-scale discrete phase domains as a result of stress concentrations that arise from the incompatibility of the materials. These shear and/or stress intensity zones cause some initial debonding in the polyolefin matrix adjacent to the micro-scale domains. Notably, however, the localized shear and/or stress intensity zones created near the nano-scale discrete phase domains may overlap with the micro-scale zones to cause even further debonding to occur in the polymer matrix, thereby creating a substantial number of nanopores adjacent to the nano-scale domains and/or micro-scale domains.

The particular nature of the microinclusion additive is not critical, and may include liquids, semi-solids, or solids (e.g., amorphous, crystalline, or semi-crystalline). In certain embodiments, the microinclusion additive is polymeric in nature and possesses a relatively high molecular weight to help improve the melt strength and stability of the thermoplastic composition. Typically, the microinclusion additive polymer may be generally incompatible with the matrix polymer. In this manner, the additive can better become dispersed as discrete phase domains within a continuous phase of the matrix polymer. The discrete domains are capable of absorbing energy that arises from an external force, which increases the overall toughness and strength of the resulting fiber. The domains may have a variety of different shapes, such as elliptical, spherical, cylindrical, plate-like, tubular, etc. In one embodiment, for example, the domains have a substantially elliptical shape. The physical dimension of an individual domain is typically small enough to minimize the propagation of cracks through the fiber upon the application of an external stress, but large enough to initiate microscopic plastic deformation and allow for shear zones at and around particle inclusions.

The microinclusion additive may have a certain melt flow rate (or viscosity) to ensure that the discrete domains and resulting pores can be adequately maintained. For example, if the melt flow rate of the additive is too high, it tends to flow and disperse uncontrollably through the continuous phase. This results in lamellar, plate-like domains or co-continuous phase structures that are difficult to maintain and also likely to prematurely fracture. Conversely, if the melt flow rate of the additive is too low, it tends to clump together and form very large elliptical domains, which are difficult to disperse during blending. This may cause uneven distribution of the additive through the entirety of the continuous phase. In this regard, the present inventors have discovered that the ratio of the melt flow rate of the microinclusion additive to the melt flow rate of the matrix polymer is typically from about 0.5 to about 10, in some embodiments from about 1 to about 8, and in some embodiments, from about 2 to about 6. The microinclusion additive may, for example, have a melt flow rate of from about 5 to about 200 grams per 10 minutes, in some embodiments from about 20 to about 150 grams per 10 minutes, and in some embodiments, from about 40 to about 100 grams per 10 minutes, determined at a load of 2160 grams and at a temperature at least about 40° C. above its melting temperature (e.g., 210° C.).

In addition to the properties noted above, the mechanical characteristics of the microinclusion additive may also be selected to achieve the desired porous network. For example, applied with an external force, stress concentrations (e.g., including normal or shear stresses) and shear and/or plastic yielding zones may be initiated at and around the discrete phase domains as a result of stress concentrations that arise from a difference in the elastic modulus of the additive and matrix polymer. Larger stress concentrations promote more intensive localized plastic flow at the domains, which allows them to become significantly elongated when stresses are imparted. These elongated domains can allow the composition to exhibit a more pliable and softer behavior. To enhance the stress concentrations, the microinclusion additive may be selected to have a relatively high Young's modulus of elasticity in comparison to the polyolefin matrix. For example, the ratio of the modulus of elasticity of the additive to that of polyolefin matrix is typically from about 1 to about 250, in some embodiments from about 2 to about 100, and in some embodiments, from about 2 to about 50. The modulus of elasticity of the microinclusion additive may, for instance, range from about 200 to about 3,500 Megapascals (MPa), in some embodiments from about 300 to about 2,000 MPa, and in some embodiments, from about 400 to about 1,500 MPa. To the contrary, the modulus of elasticity of the polyolefin may, for instance, range from about 100 to about 1,500 MPa, and in some embodiments, from about 200 to about 1000 MPa. Alternatively, the modulus of elasticity of microinclusion additive can be lower than the modulus of elasticity of polyolefin matrix. The modulus of elasticity may, for example, range from about 10 MPa to about 100 MPa, and optionally from about 20 MPA to about 80 MPa.

While a wide variety of microinclusion additives may be employed that have the properties identified above, particularly suitable examples of such additives may include styrenic copolymers (e.g., styrene-butadiene-styrene, styrene-isoprene-styrene, styrene-ethylene-propylene-styrene, styrene-ethylene-butadiene-styrene, etc.); fluoropolymers, such as polyvinyl chloride (PVC), polytetrafluoroethylene (PTFE), polychlorotrifluoroethylene (PCTFE), etc.; polyvinyl alcohols; polyvinyl acetates; polyesters, such as aliphatic polyesters, such as polycaprolactone, polyesteramides, polylactic acid (PLA) and its copolymers, polyglycolic acid, polyalkylene carbonates (e.g., polyethylene carbonate), poly-3-hydroxybutyrate (PHB), poly-3-hydroxyvalerate (PHV), poly-3-hydroxybutyrate-co-4-hydroybutyrate, poly-3-hydroxybutyrate-co-3-hydroxyvalerate copolymers (PHBV), poly-3-hydroxybutyrate-co-3-hydroxyhexanoate, poly-3-hydroxybutyrate-co-3-hydroxyoctanoate, poly-3-hydroxybutyrate-co-3-hydroxydecanoate, poly-3-hydroxybutyrate-co-3-hydroxyoctadecanoate, and succinate-based aliphatic polymers (e.g., polybutylene succinate, polybutylene succinate adipate, polyethylene succinate, etc.), aliphatic-aromatic copolyesters (e.g., polybutylene adipate terephthalate, polyethylene adipate terephthalate, polyethylene adipate isophthalate, polybutylene adipate isophthalate, etc.), aromatic polyesters (e.g., polyethylene terephthalate, polybutylene terephthalate, etc.); and so forth.

Particularly suitable are microinclusion additives that are generally rigid in nature to the extent that they have a relatively high glass transition temperature. For example, the glass transition temperature ("$T_g$") may be about 0° C. or more, in some embodiments from about 5° C. to about 100° C., in some embodiments from about 30° C. to about 80° C., and in some embodiments, from about 50° C. to about 75° C. The glass transition temperature may be determined by dynamic mechanical analysis in accordance with ASTM E1640-09.

One particularly suitable rigid polyester is polylactic acid, which may generally be derived from monomer units of any isomer of lactic acid, such as levorotory-lactic acid ("L-lactic acid"), dextrorotatory-lactic acid ("D-lactic acid"), meso-lactic acid, or mixtures thereof. Monomer units may also be formed from anhydrides of any isomer of lactic acid, including L-lactide, D-lactide, meso-lactide, or mixtures thereof. Cyclic dimers of such lactic acids and/or lactides may also be employed. Any known polymerization method, such as polycondensation or ring-opening polymerization, may be used to polymerize lactic acid. A small amount of a chain-extending agent (e.g., a diisocyanate compound, an epoxy compound or an acid anhydride) may also be employed. The polylactic acid may be a homopolymer or a copolymer, such as one that contains monomer units derived from L-lactic acid and monomer units derived from D-lactic acid. Although not required, the rate of content of one of the monomer unit derived from L-lactic acid and the monomer unit derived from D-lactic acid is preferably about 85 mole % or more, in some embodiments about 90 mole % or more, and in some embodiments, about 95 mole % or more. Multiple polylactic acids, each having a different ratio between the monomer unit derived from L-lactic acid and the monomer unit derived from D-lactic acid, may be blended at an arbitrary percentage. Of course, polylactic acid may also be blended with other types of polymers (e.g., polyolefins, polyesters, etc.).

In one particular embodiment, the polylactic acid has the following general structure:

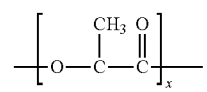

One specific example of a suitable polylactic acid polymer that may be used in the present invention is commercially available from Biomer, Inc. of Krailting, Germany) under the name BIOMER™ L9000. Other suitable polylactic acid polymers are commercially available from Natureworks LLC of Minnetonka, Minn. (NATUREWORKSO) or Mitsui Chemical (LACEA™). Still other suitable polylactic acids may be described in U.S. Pat. Nos. 4,797,468; 5,470,944; 5,770,682; 5,821,327; 5,880,254; and 6,326,458, which are incorporated herein in their entirety by reference thereto for all purposes.

The polylactic acid typically has a number average molecular weight ("$M_n$") ranging from about 40,000 to about 180,000 grams per mole, in some embodiments from about 50,000 to about 160,000 grams per mole, and in some embodiments, from about 80,000 to about 120,000 grams per mole. Likewise, the polymer also typically has a weight average molecular weight ("$M_w$") ranging from about 80,000 to about 250,000 grams per mole, in some embodiments from about 100,000 to about 200,000 grams per mole, and in some embodiments, from about 110,000 to about 160,000 grams per mole. The ratio of the weight average molecular weight to the number average molecular weight ("$M_w/M_n$"), i.e., the "polydispersity index", is also relatively low. For example, the polydispersity index typically ranges from about 1.0 to about 3.0, in some embodiments from about 1.1 to about 2.0, and in some embodiments, from about 1.2 to about 1.8. The weight and number average molecular weights may be determined by methods known to those skilled in the art.

Some types of neat polyesters (e.g., polylactic acid) can absorb water from the ambient environment such that it has a moisture content of about 500 to 600 parts per million ("ppm"), or even greater, based on the dry weight of the starting polylactic acid. Moisture content may be determined in a variety of ways as is known in the art, such as in accordance with ASTM D 7191-05, such as described below. Because the presence of water during melt processing can hydrolytically degrade the polyester and reduce its molecular weight, it is sometimes desired to dry the polyester prior to blending. In most embodiments, for example, it is desired that the renewable polyester have a moisture content of about 300 parts per million ("ppm") or less, in some embodiments about 200 ppm or less, in some embodiments from about 1 to about 100 ppm prior to blending with the microinclusion additive. Drying of the polyester may occur, for instance, at a temperature of from about 50° C. to about 100° C., and in some embodiments, from about 70° C. to about 80° C.

Regardless of the materials employed, the relative percentage of the microinclusion additive in the thermoplastic composition is selected to achieve the desired properties without significantly impacting the resulting composition. For example, the microinclusion additive is typically employed in an amount of from about 1 wt. % to about 30 wt. %, in some embodiments from about 2 wt. % to about 25 wt. %, and in some embodiments, from about 5 wt. % to about 20 wt. % of the thermoplastic composition, based on the weight of the polyolefin matrix employed in the composition. The concentration of the microinclusion additive in the entire thermoplastic composition may likewise constitute from about 0.1 wt. % to about 30 wt. %, in some embodiments from about 0.5 wt. % to about 25 wt. %, and in some embodiments, from about 1 wt. % to about 20 wt. %.

D. Other Components

A wide variety of ingredients may be employed in the composition for a variety of different reasons. For instance, in one particular embodiment, an interphase modifier may be employed in the thermoplastic composition to help reduce the degree of friction and connectivity between the nanoinclusion and/or microinclusion additives and polyolefin matrix, and thus enhance the degree and uniformity of debonding. In this manner, the pores can become distributed in a more homogeneous fashion throughout the composition. The modifier may be in a liquid or semi-solid form at room temperature (e.g., 25° C.) so that it possesses a relatively low viscosity, allowing it to be more readily incorporated into the thermoplastic composition and to easily migrate to the polymer surfaces. By reducing physical forces at the interfaces of the polyolefin matrix and the additive, it is believed that the low viscosity, hydrophobic nature of the modifier can help facilitate debonding. As used herein, the term "hydrophobic" typically refers to a material having a contact angle of water in air of about 40° or more, and in some cases, about 60° or more. In contrast, the term "hydrophilic" typically refers to a material having a contact angle of water in air of less than about 40°. One suitable test for measuring the contact angle is ASTM D5725-99 (2008).

Although not required, the interphase modifier may be particularly suitable in embodiments in which a microinclusion additive is employed and in which the nanoinclusion additive is a solid (e.g., polymeric material). Suitable hydrophobic, low viscosity interphase modifiers may include, for instance, the liquids and/or semi-solids referenced above. One particularly suitable interphase modifier is polyether polyol, such as commercially available under the trade name PLURIOL® WI from BASF Corp. Another suitable modifier is a partially renewable ester, such as commercially available under the trade name HALLGREEN® IM from Hallstar.

When employed, the interphase modifier may constitute from about 0.1 wt. % to about 20 wt. %, in some embodiments from about 0.5 wt. % to about 15 wt. %, and in some embodiments, from about 1 wt. % to about 10 wt. % of the thermoplastic composition, based on the weight of the continuous phase polyolefin matrix. The concentration of the interphase modifier in the entire thermoplastic composition may likewise constitute from about 0.05 wt. % to about 20 wt. %, in some embodiments from about 0.1 wt. % to about 15 wt. %, and in some embodiments, from about 0.5 wt. % to about 10 wt. %. In the amounts noted above, the interphase modifier has a character that enables it to readily migrate to the interfacial surface of the polymers and facilitate debonding without disrupting the overall melt properties of the thermoplastic composition. For example, the melt flow rate of the thermoplastic composition may also be similar to that of the polyolefin matrix. For example, the melt flow rate of the composition (on a dry basis) may be from about 0.1 to about 250 grams per 10 minutes, in some embodiments from about 0.5 to about 200 grams per 10 minutes, and in some embodiments, from about 5 to about 150 grams per 10 minutes, determined at a load of 2160 grams and at 190° C. in accordance with ASTM D1238.

Compatibilizers may also be employed that improve interfacial adhesion and reduce the interfacial tension between the domain and the matrix, thus allowing the formation of smaller domains during mixing. Examples of suitable compatibilizers may include, for instance, copolymers functionalized with epoxy or maleic anhydride chemical moieties. An example of a maleic anhydride compatibilizer is polypropylene-grafted-maleic anhydride, which is commercially available from Arkema under the trade names Orevac™ 18750 and Orevac™ CA 100. When employed, compatibilizers may constitute from about 0.05 wt. % to about 10 wt. %, in some embodiments from about 0.1 wt. % to about 8 wt. %, and in some embodiments, from about 0.5 wt. % to about 5 wt. % of the thermoplastic composition, based on the weight of the continuous phase matrix.

Other suitable materials that may also be used in the thermoplastic composition, such as catalysts, antioxidants, stabilizers, surfactants, waxes, solid solvents, nucleating agents, particulates, nanofillers, and other materials added to enhance the processability and mechanical properties of the thermoplastic composition. Nevertheless, one beneficial aspect of the present invention is that good properties may be provided without the need for various conventional additives, such as blowing agents (e.g., chlorofluorocarbons, hydrochlorofluorocarbons, hydrocarbons, carbon dioxide, supercritical carbon dioxide, nitrogen, etc.) and pore-initiating fillers (e.g., calcium carbonate). In fact, the thermoplastic composition may be generally free of blowing agents and/or pore-initiating fillers. For example, such blowing agents and/or fillers may be present in an amount of no more than about 1 wt. %, in some embodiments no more than about 0.5 wt. %, and in some embodiments, from about 0.001 wt. % to about 0.2 wt. % of the thermoplastic composition. Further, due to its stress whitening properties, as described in more detail below, the resulting composition may achieve an opaque color (e.g., white) without the need for conventional pigments, such as titanium dioxide. In certain embodiments, for example, pigments may be present in an amount of no more than about 1 wt. %, in some embodiments no more than about 0.5 wt. %, and in some embodiments, from about 0.001 wt. % to about 0.2 wt. % of the thermoplastic composition.

II. Blending

To form the thermoplastic composition, the components are typically blended together using any of a variety of known techniques. In one embodiment, for example, the components may be supplied separately or in combination. For instance, the components may first be dry mixed together to form an essentially homogeneous dry mixture, and they may likewise be supplied either simultaneously or in sequence to a melt processing device that dispersively blends the materials. Batch and/or continuous melt processing techniques may be employed. For example, a mixer/kneader, Banbury mixer, Farrel continuous mixer, single-screw extruder, twin-screw extruder, roll mill, etc., may be utilized to blend and melt process the materials. Particularly suitable melt processing devices may be a co-rotating, twin-screw extruder (e.g., ZSK-30 extruder available from Wemer & Pfleiderer Corporation of Ramsey, N.J. or a Thermo Prism™ USALAB 16 extruder available from Thermo Electron Corp., Stone, England). Such extruders may include feeding and venting ports and provide high intensity distributive and dispersive mixing. For example, the components may be fed to the same or different feeding ports of the twin-screw extruder and melt blended to form a substantially homogeneous melted mixture. If desired, other additives may also be injected into the polymer melt and/or separately fed into the extruder at a different point along its length.

Regardless of the particular processing technique chosen, the resulting melt blended composition typically contains nano-scale domains of the nanoinclusion additive and optionally micro-scale domains of the microinclusion additive. The degree of shear/pressure and heat may be controlled to ensure sufficient dispersion, but not so high as to adversely reduce the size of the domains so that they are incapable of achieving the desired properties. For example, blending typically occurs at a temperature of from about 180° C. to about 300° C., in some embodiments from about 185° C. to about 250° C., and in some embodiments, from about 190° C. to about 240° C. Likewise, the apparent shear rate during melt processing may range from about 10 seconds$^{-1}$ to about 3000 seconds$^{-1}$, in some embodiments from about 50 seconds$^{-1}$ to about 2000 seconds$^{-1}$, and in some embodiments, from about 100 seconds$^{-1}$ to about 1200 seconds$^{-1}$. The apparent shear rate may be equal to $4Q/\pi R^3$, where Q is the volumetric flow rate ("m$^3$/s") of the polymer melt and R is the radius ("m") of the capillary (e.g., extruder die) through which the melted polymer flows. Of course, other variables, such as the residence time during melt processing, which is inversely proportional to throughput rate, may also be controlled to achieve the desired degree of homogeneity.

To achieve the desired shear conditions (e.g., rate, residence time, shear rate, melt processing temperature, etc.), the speed of the extruder screw(s) may be selected with a certain range. Generally, an increase in product temperature is observed with increasing screw speed due to the additional mechanical energy input into the system. For example, the screw speed may range from about 50 to about 600 revolutions per minute ("rpm"), in some embodiments from about 70 to about 500 rpm, and in some embodiments, from about 100 to about 300 rpm. This may result in a temperature that is sufficiently high to disperse the nanoinclusion additive without adversely impacting the size of the resulting domains. The melt shear rate, and in turn the degree to which the additives are dispersed, may also be increased through the use of one or more distributive and/or dispersive mixing elements within the mixing section of the extruder. Suitable distributive mixers for single screw extruders may include, for instance, Saxon, Dulmage, Cavity Transfer mixers, etc. Likewise, suitable dispersive mixers may include Blister ring, Leroy/Maddock, CRD mixers, etc. As is well known in the art, the mixing may be further improved by using pins in the barrel that create a folding and reorientation of the polymer melt, such as those used in Buss Kneader extruders, Cavity Transfer mixers, and Vortex Intermeshing Pin (VIP) mixers.

III. Fiber Formation

As used herein, the term "fiber" generally refers to an elongated extrudate formed by passing a polymer through a forming orifice, such as a die. Unless noted otherwise, the term "fiber" includes both discontinuous fibers having a definite length and substantially continuous filaments. Substantially filaments may, for instance, have a length much greater than their diameter, such as a length to diameter ratio ("aspect ratio") greater than about 15,000 to 1, and in some cases, greater than about 50,000 to 1.

Fibers formed from the thermoplastic composition may generally have any desired configuration, including monocomponent and multicomponent (e.g., sheath-core configuration, side-by-side configuration, segmented pie configuration, island-in-the-sea configuration, and so forth). Hollow fibers (monocomponent and/or multicomponent) may also be employed, such as described in U.S. Pat. No. 6,642,429 to Carter, et al. In some embodiments, the fibers may contain one or more additional polymers as a component (e.g., bicomponent) or constituent (e.g., biconstituent) to further enhance strength, processability, and/or other properties. For instance, the thermoplastic composition may form a core component of a sheath/core bicomponent fiber, while an additional polymer may form the sheath component, or vice versa. The additional polymer may be any polymer desired, such as polyesters, e.g., polylactic acid, polyethylene terephthalate, etc.; polyolefins, e.g., polyethylene, polypropylene, polybutylene, and so forth; polytetrafluoroethylene;

polyvinyl acetate; polyvinyl chloride acetate; polyvinyl butyral; acrylic resins, e.g., polyacrylate, polymethylacrylate, polymethylmethacrylate, and so forth; polyamides, e.g., nylon; polyvinyl chloride; polyvinylidene chloride; polystyrene; polyvinyl alcohol; and polyurethanes.

Any of a variety of processes may be used to form fibers in accordance with the present invention. For example, the thermoplastic composition described above may be extruded through a spinneret and quenched. Referring to FIG. 9, for example, one embodiment of a method for forming fibers is shown in more detail. In this particular embodiment, the thermoplastic composition of the present invention may be fed into an extruder 12 from a hopper 14. The blend may be provided to the hopper 14 using any conventional technique. The extruder 12 is heated to a temperature sufficient to extrude the melted polymer. The extruded composition is then passed through a polymer conduit 16 to a spinneret 18. For example, the spinneret 18 may include a housing containing a spin pack having a plurality of plates stacked one on top of each other and having a pattern of openings arranged to create flow paths for directing polymer components. The spinneret 18 also has openings arranged in one or more rows. The openings form a downwardly extruding curtain of filaments when the polymers are extruded therethrough. The process 10 also employs a quench blower 20 positioned adjacent the curtain of fibers extending from the spinneret 18. Air from the quench air blower 20 quenches the fibers extending from the spinneret 18. The quench air may be directed from one side of the fiber curtain as shown in FIG. 9 or both sides of the fiber curtain.

To form a fiber with the desired length, the quenched fibers are generally melt drawn, such as using a fiber draw unit 22 as shown in FIG. 9. Fiber draw units or aspirators for use in melt spinning polymers are well-known in the art. Suitable fiber draw units for use in the process of the present invention include a linear fiber aspirator of the type shown in U.S. Pat. Nos. 3,802,817 and 3,423,255. The fiber draw 22 generally includes an elongated vertical passage through which the fibers are drawn by aspirating air entering from the sides of the passage and flowing downwardly through the passage. A heater or blower 24 supplies aspirating air to the fiber draw unit 22. The aspirating air melt draws the fibers and ambient air through the fiber draw unit 22. The flow of gas causes the fibers to melt draw or attenuate, which increases the molecular orientation or crystallinity of the polymers forming the fibers. When employing a fiber draw unit, the "draw down" ratio may be selected to help achieve the desired fiber length. The "drawn down" ratio is the linear speed of the fibers after drawing (e.g., linear speed of the godet roll 42 or a foraminous surface (not shown) divided by the linear speed of the fibers after extrusion). For example, the draw down ratio during melt drawing may be calculated as follows:

$$\text{Draw Down Ratio} = A/B$$

wherein,

A is the linear speed of the fiber after melt drawing (e.g., godet speed) and is directly measured; and B is the linear speed of the extruded fiber and can be calculated as follows:

$$\text{Extruder linear fiber speed} = C/(25 * \pi * D * E^2)$$

wherein,

C is the throughput through a single hole (grams per minute);

D is the melt density of the polymer (grams per cubic centimeter); and

E is the diameter of the orifice (in centimeters) through which the fiber is extruded. In certain embodiments, the draw down ratio may be from about 20:1 to about 4000:1, in some embodiments from about 25:1 to about 2000:1, and in some embodiments, from about 50:1 to about 1000:1 and in some embodiments from about 75:1 to about 800:1.

Once formed, the fibers may be deposited through the outlet opening of the fiber draw unit 22 and onto a godet roll 42. If desired, the fibers collected on the godet roll 42 may optionally be subjected to additional in line processing and/or converting steps (not shown) as will be understood by those skilled in the art. For example, fibers may be collected and thereafter crimped, texturized, and/or and cut to an average fiber length in the range of from about 3 to about 80 millimeters, in some embodiments from about 4 to about 65 millimeters, and in some embodiments, from about 5 to about 50 millimeters. The staple fibers may then be incorporated into a nonwoven web as is known in the art, such as bonded carded webs, through-air bonded webs, etc. The fibers may also be deposited onto a foraminous surface to form a nonwoven web, such as described in more detail below.

Regardless of the particular manner in which they are formed, the resulting fibers may be drawn to form the desired porous network. If desired, the fibers may be drawn in-line as the fibers are being formed. Alternatively, the fibers may be drawn in their solid state after they are formed. By "solid state" drawing, it is generally meant that the composition is kept at a temperature below the melting temperature of the polyolefin matrix polymer. Among other things, this helps to ensure that the polymer chains are not altered to such an extent that the porous network becomes unstable. For example, the composition may be drawn at a temperature of from about 0° C. to about 50° C., in some embodiments from about 15° C. to about 40° C., and in some embodiments, from about 20° C. to about 30° C. This may optionally be at least about 10° C., in some embodiments at least about 20° C., and in some embodiments, at least about 30° C. below the glass transition temperature of the component having the highest glass transition temperature (e.g., microinclusion additive). In certain embodiments, for example, drawing may occur at a temperature of from about −50° C. to about 150° C., in some embodiments from about −40° C. to about 100° C., and in some embodiments, from about −20° C. to about 50° C.

Drawing of the fibers may occur in one or multiple stages. In one embodiment, for example, drawing is completed in-line without having to remove it for separate processing. In FIG. 9, for instance, the fibers may be initially melt drawn by the fiber draw unit 22, transferred to a nip (not shown) where the matrix polymer is allowed to cool below its melting temperature, and thereafter subjected to an additional drawing step before being deposited on the godet roll 42. In other cases, however, the fibers may be removed from the fiber forming machinery and subjected to an additional drawing step. Regardless, various drawing techniques may be employed, such as aspiration (e.g., fiber draw units), tensile frame drawing, biaxial drawing, multi-axial drawing, profile drawing, vacuum drawing, etc. The composition is typically drawn (e.g., in the machine direction) to a draw ratio of from about 1.1 to about 3.5, in some embodiments from about 1.2 to about 3.0, and in some embodiments, from about 1.3 to about 2.5. The draw ratio may be determined by dividing the length of the drawn fiber by its length before drawing. The draw rate may also vary to help achieve the desired properties, such as within the range of from about 5% to about 1500% per minute of deformation, in some embodiments from about 20% to about 1000% per minute of deformation, and in some embodiments, from about 25% to about 850% per minute of deformation. Although the composition is typically drawn without the application of external heat (e.g., heated rolls), such heat might be optionally employed to improve processability, reduce draw force, increase draw rates, and improve fiber uniformity.

Drawing in the manner described above can result in the formation of pores having a "nano-scale" dimension ("nanopores"), such as an average cross-sectional dimension of about 800 nanometers or less, in some embodiments from about 5 to about 700 nanometers, and in some embodiments, from about 10 to about 500 nanometers. The nanopores may also have an average axial dimension (e.g., length) of from about 100 to about 5000 nanometers, in some embodiments from about 50 to about 2000 nanometers, and in some embodiments, from about 100 to about 1000 nanometers. Micropores may also be formed during drawing that have an average cross-sectional dimension of about 0.2 micrometers or more, in some embodiments about 0.5 micrometers or more, and in some embodiments, from about 0.5 micrometers to about 5 micrometers. In certain cases, the axial dimension of the micropores and/or nanopores may be larger than the cross-sectional dimension so that the aspect ratio (the ratio of the axial dimension to the cross-sectional dimension) is from about 1 to about 30, in some embodiments from about 1.1 to about 15, and in some embodiments, from about 1.2 to about 5. For example, the axial dimension of the micropores may be 1 micrometer or more, in some embodiments about 1.5 micrometers or more, and in some embodiments, from about 2 to about 30 micrometers.

Regardless of their particular size, the present inventors have discovered that the pores (e.g., nanopores, micropores, or both) can be distributed in a substantially homogeneous fashion throughout the composition. For example, the pores may be distributed in columns that are oriented in a direction generally perpendicular to the direction in which a stress is applied. These columns may be generally parallel to each other across the width of the composition. Without intending to be limited by theory, it is believed that the presence of such a homogeneously distributed porous network can result in good mechanical properties (e.g., energy dissipation under load and impact strength). This is in stark contrast to conventional techniques for creating pores that involve the use of blowing agents, which tend to result in an uncontrolled pore distribution and poor mechanical properties.

In addition to forming a porous network, drawing can also significantly increase the axial dimension of certain of the discrete domains so that they have a generally linear, elongated shape. For example, the elongated micro-scale domains may have an axial dimension that is about 10% or more, in some embodiments from about 20% to about 500%, and in some embodiments, from about 50% to about 250% greater than the axial dimension of the domains prior to drawing. The axial dimension (e.g., length) after drawing may, for instance, range from about 1 μm to about 400 μm, in some embodiments from about 5 μm to about 200 μm, and in some embodiments from about 10 μm to about 150 μm. The micro-scale domains may also be relatively thin and thus have a small cross-sectional dimension, such as from about 0.02 to about 20 micrometers, in some embodiments from about 0.1 to about 10 micrometers, and in some embodiments, from about 0.4 to about 5 micrometers. This may result in an aspect ratio for the domains (the ratio of the axial dimension to a dimension orthogonal to the axial dimension) of from about 2 to about 150, in some embodiments from about 3 to about 100, and in some embodiments, from about 4 to about 50. Due to their small size, the nano-scale domains are not typically elongated in the same manner as the micro-scale domains. Thus, the nano-scale domains may retain an average axial dimension (e.g., length) of from about 1 to about 1000 nanometers, in some embodiments from about 5 to about 800 nanometers, in some embodiments from about 10 to about 500 nanometers, and in some embodiments from about 20 to about 200 nanometers.

Drawing may also create one or more localized necked regions along the longitudinal axis of the fiber, which are spaced between unnecked regions. The necked fibers may also possess a non-uniform, cross-sectional diameter along its longitudinal axis, which can provide a variety of different benefits, such as increased surface area, etc. The number of necked regions may generally vary and may be controlled based on the selected stretch ratio. Typically, however, the number of necked regions may range from about 1 to about 400 necks per centimeter, in some embodiments from about 2 to about 200 necks per centimeter, and in some embodiments, from about 5 to about 50 necks per centimeter. The number of necked regions may be determined from the following equation:

$$N = (1-L_2)/(L+L_2)$$

where, N is the number of necked regions, $L_1$ is the average length of a necked region, and $L_2$ is the average length of an unnecked region (includes transition from necked to unnecked region.

Even at the very low densities achieved by the present invention, the resulting fibers are not brittle and thus can deform upon the application of strain, rather than fracture. The fibers may thus continue to function as a load bearing member even after the fiber has exhibited substantial elongation. In this regard, the fibers of the present invention are capable of exhibiting improved "peak elongation properties, i.e., the percent elongation of the fiber at its peak load. For example, the fibers of the present invention may exhibit a peak elongation of about 50% or more, in some embodiments about 100% or more, in some embodiments from about 200% to about 1500%, and in some embodiments, from about 400% to about 800%, such as determined in accordance with ASTM D638-10 at 23° C. Such elongations may be achieved for fibers having a wide variety of average diameters, such as those ranging from about 0.1 to about 50 micrometers, in some embodiments from about 1 to about 40 micrometers, in some embodiments from about 2 to about 25 micrometers, and in some embodiments, from about 5 to about 15 micrometers.

While possessing the ability to extend under strain, the fibers of the present invention can also remain relatively strong. For example, the fibers may exhibit a peak tensile stress of from about 25 to about 600 Megapascals ("MPa"), in some embodiments from about 50 to about 450 MPa, and in some embodiments, from about 60 to about 350 MPa, such as determined in accordance with ASTM D638-10 at 23° C. Another parameter that is indicative of the relative strength of the fibers of the present invention is "tenacity", which indicates the tensile strength of a fiber expressed as force per unit linear density. For example, the fibers of the present invention may have a tenacity of from about 0.75 to about 7.0 grams-force ("$g_f$") per denier, in some embodiments from about 1.0 to about 6.0 $g_f$ per denier, and in some embodiments, from about 1.5 to about 5.0 $g_f$ per denier. The denier of the fibers may vary depending on the desired application. Typically, the fibers are formed to have a denier per filament (i.e., the unit of linear density equal to the mass in grams per 9000 meters of fiber) of less than about 15, in some embodiments less than about 12, and in some embodiments, from about 0.5 to about 6.

III. Nonwoven Web

The fibers may be formed into a nonwoven web structure by randomly depositing the fibers onto a forming surface (optionally with the aid of a vacuum) and then bonding the resulting web using any known technique. The nonwoven web may be formed before or after the fibers are drawn. In certain embodiments, for instance, it may be desired to form a nonwoven web from a plurality of fibers, and thereafter draw the fibers by stretching the nonwoven web to the extent desired to form the porous network. In an alternative embodiment, an endless forming surface may simply be positioned below a fiber aspiration unit that draws the fibers to the desired extent before the web is formed.

Once formed, the nonwoven web may then be bonded using any conventional technique, such as with an adhesive or autogeneously (e.g., fusion and/or self-adhesion of the fibers without an applied external adhesive). Autogenous bonding, for instance, may be achieved through contact of the fibers while they are semi-molten or tacky, or simply by blending a tackifying resin and/or solvent with the polymer used to form the fibers. Suitable autogenous bonding techniques may include ultrasonic bonding, thermal bonding, through-air bonding, calendar bonding, and so forth. For example, the web may be further bonded or embossed with a pattern by a thermo-mechanical process in which the web is passed between a heated smooth anvil roll and a heated pattern roll. The pattern roll may have any raised pattern which provides the desired web properties or appearance. Desirably, the pattern roll defines a raised pattern which defines a plurality of bond locations which define a bond area between about 2% and 30% of the total area of the roll. Exemplary bond patterns include, for instance, those described in U.S. Pat. No. 3,855,046 to Hansen et al., U.S. Pat. No. 5,620,779 to Lew et al., U.S. Pat. No. 5,962,112 to Haynes et al., U.S. Pat. No. 6,093,665 to Sayovitz et al., as well as U.S. Design Pat. Nos. 428,267 to Romano et al.; 390,708 to Brown; 418,305 to Zander, et al.; 384,508 to Zander, et al.; 384,819 to Zander, et al.; 358,035 to Zander, et al.; and 315,990 to Blenke, et al. The pressure between the rolls may be from about 5 to about 2000 pounds per lineal inch. The pressure between the rolls and the temperature of the rolls is balanced to obtain desired web properties or appearance while maintaining cloth like properties. As is well known to those skilled in the art, the temperature and pressure required may vary depending upon many factors including but not limited to, pattern bond area, polymer properties, fiber properties and nonwoven properties.

In addition to spunbond webs, a variety of other nonwoven webs may also be formed from the thermoplastic composition in accordance with the present invention, such as meltblown webs, bonded carded webs, wet-laid webs, airlaid webs, coform webs, hydraulically entangled webs, etc. For example, the thermoplastic composition may be extruded through a plurality of fine die capillaries into a converging high velocity gas (e.g., air) streams that attenuate the fibers to reduce their diameter. Thereafter, the meltblown fibers are carried by the high velocity gas stream and are deposited on a collecting surface to form a web of randomly dispersed meltblown fibers. Alternatively, the polymer may be formed into a carded web by placing bales of fibers formed from the thermoplastic composition into a picker that separates the fibers. Next, the fibers are sent through a combing or carding unit that further breaks apart and aligns the fibers in the machine direction so as to form a machine direction-oriented fibrous nonwoven web. Once formed, the nonwoven web is typically stabilized by one or more known bonding techniques as described above to form a bonded carded web.

If desired, the nonwoven web may also be a composite that contains a combination of the fibers of the present invention and other types of fibers (e.g., staple fibers, filaments, etc.). For example, additional synthetic fibers may be utilized, such as those formed from polyolefins, e.g., polyethylene, polypropylene, polybutylene, and so forth; polytetrafluoroethylene; polyesters, e.g., polyethylene terephthalate and so forth; polyvinyl acetate; polyvinyl chloride acetate; polyvinyl butyral; acrylic resins, e.g., polyacrylate, polymethylacrylate, polymethylmethacrylate, and so forth; polyamides, e.g., nylon; polyvinyl chloride; polyvinylidene chloride; polystyrene; polyvinyl alcohol; polyurethanes; polylactic acid; etc. If desired, renewable polymers may also be employed. Some examples of known synthetic fibers include sheath-core bicomponent fibers available from KoSa Inc. of Charlotte, N.C. under the designations T-255 and T-256, both of which use a polyolefin sheath, or T-254, which has a low melt co-polyester sheath. Still other known bicomponent fibers that may be used include those available from the Chisso Corporation of Moriyama, Japan or Fibervisions LLC of Wilmington, Del. Polylactic acid staple fibers may also be employed, such as those commercially available from Far Eastern Textile, Ltd. of Taiwan.

The composite may also contain pulp fibers, such as high-average fiber length pulp, low-average fiber length pulp, or mixtures thereof. One example of suitable high-average length fluff pulp fibers includes softwood kraft pulp fibers. Softwood kraft pulp fibers are derived from coniferous trees and include pulp fibers such as, but not limited to, northern, western, and southern softwood species, including redwood, red cedar, hemlock, Douglas fir, true firs, pine (e.g., southern pines), spruce (e.g., black spruce), bamboo, combinations thereof, and so forth. Northern softwood kraft pulp fibers may be used in the present invention. An example of commercially available southern softwood kraft pulp fibers suitable for use in the present invention include those available from Weyerhaeuser Company with offices in Federal Way, Washington under the trade designation of "NF-405." Another suitable pulp for use in the present invention is a bleached, sulfate wood pulp containing primarily softwood fibers that is available from Bowater Corp. with offices in Greenville, S.C. under the trade name CoosAbsorb S pulp. Low-average length fibers may also be used in the present invention. An example of suitable low-average length pulp fibers is hardwood kraft pulp fibers. Hardwood kraft pulp fibers are derived from deciduous trees and include pulp fibers such as, but not limited to, eucalyptus, maple, birch, aspen, etc. Eucalyptus kraft pulp fibers may be particularly desired to increase softness, enhance brightness, increase opacity, and change the pore structure of the sheet to increase its wicking ability. Bamboo or cotton fibers may also be employed.

Nonwoven composites may be formed using a variety of known techniques. For example, the nonwoven composite may be a "coform material" that contains a mixture or stabilized matrix of the thermoplastic composition fibers and an absorbent material. As an example, coform materials may be made by a process in which at least one meltblown die head is arranged near a chute through which the absorbent materials are added to the web while it is forming. Such absorbent materials may include, but are not limited to, pulp fibers, superabsorbent particles, inorganic and/or organic absorbent materials, treated polymeric staple fibers, and so forth. The relative percentages of the absorbent material may vary over a wide range depending on the desired characteristics of the nonwoven composite. For example, the nonwoven composite may contain from about 1 wt. % to about 60 wt. %, in some embodiments from 5 wt. % to about 50 wt. %, and in some embodiments, from about 10 wt. % to about 40 wt. % thermoplastic composition fibers. The nonwoven composite may likewise contain from about 40 wt. % to about 99 wt. %, in some embodiments from 50 wt. % to about 95 wt. %, and in some embodiments, from about 60 wt. % to about 90 wt. % absorbent material. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.

Nonwoven laminates may also be formed in the present invention in which one or more layers are formed from the thermoplastic composition. For example, the nonwoven web of one layer may be a spunbond that contains the thermoplastic composition, while the nonwoven web of another layer contains thermoplastic composition, other renewable polymer(s), and/or any other polymer (e.g., polyolefins). In one embodiment, the nonwoven laminate contains a meltblown layer positioned between two spunbond layers to form a spunbond/meltblown/spunbond ("SMS") laminate. If desired, the spunbond layer(s) may be formed from the thermoplastic composition. The meltblown layer may be formed from the thermoplastic composition, other renewable polymer(s), and/or any other polymer (e.g., polyolefins) . Various techniques for forming SMS laminates are described in U.S. Pat. No. 4,041,203 to Brock et al.; U.S. Pat. No. 5,213,881 to Timmons, et al.; U.S. Pat. No. 5,464,688 to Timmons, et al.; U.S. Pat. No. 4,374,888 to Bornslaeger; U.S. Pat. No. 5,169,706 to Collier, et al.; and U.S. Pat. No. 4,766,029 to Brock et al., as well as U.S. Patent Application Publication No. 2004/0002273 to Fitting, et al. Of course, the nonwoven laminate may have other configuration and possess any desired number of meltblown and spunbond layers, such as spunbond/meltblown/meltblown/spunbond laminates ("SMMS"), spunbond/meltblown laminates ("SM"), etc. Although the basis weight of the nonwoven laminate may be tailored to the desired application, it generally ranges from about 10 to about 300 grams per square meter ("gsm"), in some embodiments from about 25 to about 200 gsm, and in some embodiments, from about 40 to about 150 gsm.

Nonwoven-film laminates may also be formed. In such embodiments, the film is typically liquid-impermeable and either vapor-permeable or vapor-impermeable. Films that are liquid-impermeable and vapor-permeable are often referred to as "breathable" and they typically have a water vapor transmission rate ("WVTR") of about 100 grams per square meter per 24 hours (g/m$^2$/24 hours) or more, in some embodiments from about 500 to about 20,000 g/m$^2$/24 hours, and in some embodiments, from about 1,000 to about 15,000 g g/m$^2$/24 hours. The breathable film may also be a microporous or monolithic film. Microporous films are typically formed by incorporating a filler (e.g., calcium carbonate) into the polymer matrix, and thereafter stretching the film to create the pores. Examples of such films are described, for instance, in U.S. Pat. No. 5,843,057 to McCormack; U.S. Pat. No. 5,855,999 to McCormack; U.S. Pat. No. 5,932,497 to Morman, et al.; U.S. Pat. No. 5,997,981 to McCormack, et al.; U.S. Pat. No. 6,002,064 to Kobylivker, et al.; U.S. Pat. No. 6,015,764 to McCormack, et al.; U.S. Pat. No. 6,037,281 to Mathis, et al.; U.S. Pat. No. 6,111,163 to McCormack, et al.; and U.S. Pat. No. 6,461,457 to Taylor, et al.

If desired, the fibers, nonwoven web, etc., may also be annealed to help ensure that they retains the desired shape. Annealing typically occurs at temperatures of from about 40° C. to about 120° C., in some embodiments from about 50° C. to about 110° C., and in some embodiments, from about 80° C. to about 100° C. The fibers may also be surface treated using any of a variety of known techniques to improve its properties. For example, high energy beams (e.g., plasma, x-rays, e-beam, etc.) may be used to remove or reduce any skin layers that form on the fibers, to change the surface polarity, embrittle a surface layer, etc. If desired, such surface treatment may be used before and/or after formation of a web, as well as before and/or after cold drawing of the fibers.

Besides a reduced density, the nanoporous structure may also provide a variety of additional different benefits to the nonwoven web containing the polyolefin fibers of the present invention. For example, the nanoporous structure can help restrict the flow of fluids and be generally impermeable to fluids (e.g., liquid water), thereby allowing the nonwoven web to insulate a surface from water penetration. In this regard, the fibrous material may have a relatively high hydrohead value of about 50 centimeters ("cm") or more, in some embodiments about 100 cm or more, in some embodiments, about 150 cm or more, and in some embodiments, from about 200 cm to about 1000 cm, as determined in accordance with ATTCC 127-2008. Other beneficial properties may also be achieved. For example, the nonwoven web may be generally permeable to water vapors. The permeability of a fibrous material to water vapor may characterized by its relatively high water vapor transmission rate ("WVTR"), which is the rate at which water vapor permeates through a material as measured in units of grams per meter squared per 24 hours (g/m$^2$/24 hrs). For example, the nonwoven web may exhibit a WVTR of about 300 g/m$^2$-24 hours or more, in some embodiments about 500 g/m$^2$-24 hours or more, in some embodiments about 1,000 g/m$^2$-24 hours or more, and in some embodiments, from about 3,000 to about 15,000 g/m$^2$-24 hours, such as determined in accordance with ASTM E96/96M-12, Procedure B or INDA Test Procedure IST-70.4 (01).

IV. Absorbent Article

Due to its unique and beneficial properties, the nonwoven web of the present invention is particularly well suited for use in a layer and/or component of an absorbent article. Absorbent articles, for instance, generally include an absorbent member (e.g., core layer, surge layer, transfer delay layer, wrapsheet, ventilation layer, etc.) positioned between a backsheet and a topsheet. The absorbent article may also contain other components as is known in the art, such as side panels, containment flaps, ears, waist or leg bands, etc. Generally speaking, the nonwoven web of the present invention may be employed in any layer or component of the absorbent article, such as the topsheet, backsheet, and/or absorbent member. When employed in certain layers or components (e.g., backsheet), it may be desirable to laminate the nonwoven web of the present invention to a film as described above.

In this regard, various exemplary embodiments of the absorbent article will be described. Referring to FIG. 1, for instance, one particular embodiment of an absorbent article 201 is shown in the form of a diaper. However, as noted above, the invention may be embodied in other types of absorbent articles, such as incontinence articles, sanitary napkins, diaper pants, feminine napkins, training pants, and so forth. In the illustrated embodiment, the absorbent article 201 is shown as having an hourglass shape in an unfastened configuration. However, other shapes may of course be utilized, such as a generally rectangular shape, T-shape, or I-shape. As shown, the absorbent article 201 includes a chassis 202 formed by various components, including a backsheet 217, topsheet 205, and absorbent member that includes an absorbent core layer 203 and surge layer 207. It should be understood, however, that other layers may also be used in the present invention. Likewise, one or more of the layers referred to in FIG. 1 may also be eliminated in certain embodiments of the present invention.

As indicated above, the backsheet 217 may contain the nonwoven web of the present invention. If desired, the nonwoven web may be positioned so that it defines a garment-facing surface 333 of the absorbent article 201. The absorbent article 201 also includes a topsheet 205. The topsheet 205 is generally designed to contact the body of the user and is liquid-permeable. For example, the topsheet 205 may define a body-facing surface 218, which is typically compliant, soft feeling, and non-irritating to the wearer's skin. If desired, the topsheet 205 may contain the nonwoven web of the present invention. For example, the nonwoven web may be positioned so that it defines the body-facing surface 218 if so desired. The topsheet may surround the absorbent core layer 203 so that it completely encases the absorbent article. Alternatively, the topsheet 205 and the backsheet 217 may extend beyond the absorbent member and be peripherally joined together, either entirely or partially, using known techniques, such as by adhesive bonding, ultrasonic bonding, etc. As indicated above, the topsheet 205 may include the nonwoven web of the present invention. The topsheet 205 may also include a conventional a nonwoven web (e.g., spunbond web, meltblown web, or bonded carded web). Other exemplary topsheet constructions that contain a nonwoven web are described in U.S. Pat. Nos. 5,192,606; 5,702,377; 5,931,823; 6,060,638; and 6,150,002, as well as U.S. Patent Application Publication Nos. 2004/0102750, 2005/0054255, and 2005/0059941. The topsheet 205 may also contain a plurality of apertures formed therethrough to permit body fluid to pass more readily into the absorbent core layer 203. The apertures may be randomly or uniformly arranged throughout the topsheet 205, or they may be located only in the narrow longitudinal band or strip arranged along the longitudinal axis of the absorbent article. The apertures permit rapid penetration of body fluid down into the absorbent member. The size, shape, diameter and number of apertures may be varied to suit one's particular needs.

The absorbent article also contains an absorbent member positioned between the topsheet and the backsheet. The absorbent member may be formed from a single absorbent layer or a composite containing separate and distinct absorbent layer. It should be understood, however, that any number of absorbent layers may be utilized in the present invention. In FIG. 1, for instance, the absorbent member contains an absorbent core layer 203 and a surge layer 207 that helps to decelerate and diffuse surges or gushes of liquid that may be rapidly introduced into the absorbent core layer 203. Desirably, the surge layer 207 rapidly accepts and temporarily holds the liquid prior to releasing it into the storage or retention portions of the absorbent core layer 203. In the illustrated embodiment, for example, the surge layer 207 is interposed between an inwardly facing surface 216 of the topsheet 205 and the absorbent core layer 203. Alternatively, the surge layer 207 may be located on the outwardly facing surface 218 of the topsheet 205. The surge layer 207 is typically constructed from highly liquid-permeable materials. Suitable materials may include porous woven materials, porous nonwoven materials, and apertured films. In one embodiment, the surge layer 207 may contain the nonwoven web of the present invention. Other examples of suitable surge layers are described in U.S. Pat. No. 5,486,166 to Ellis, et al. and U.S. Pat. No. 5,490,846 to Ellis, et al.

If desired, the absorbent member may also contain a transfer delay layer positioned vertically below the surge layer. The transfer delay layer may contain a material that is less hydrophilic than the other absorbent layers, and may generally be characterized as being substantially hydrophobic. For example, the transfer delay layer may be a nonwoven web (e.g., spunbond web) formed according to the present invention. The fibers may be round, tri-lobal or poly-lobal in cross-sectional shape and which may be hollow or solid in structure. Typically the webs are bonded, such as by thermal bonding, over about 3% to about 30% of the web area. Other examples of suitable materials that may be used for the transfer delay layer are described in U.S. Pat. No. 4,798,603 to Meyer. et al. and U.S. Pat. No. 5,248,309 to Serbiak, et al. To adjust the performance of the invention, the transfer delay layer may also be treated with a selected amount of surfactant to increase its initial wettability.

The transfer delay layer may generally have any size, such as a length of about 150 mm to about 300 mm. Typically, the length of the transfer delay layer is approximately equal to the length of the absorbent article. The transfer delay layer may also be equal in width to the surge layer, but is typically wider. For example, the width of the transfer delay layer may be from between about 50 mm to about 75 mm, and particularly about 48 mm. The transfer delay layer typically has a basis weight less than that of the other absorbent members. For example, the basis weight of the transfer delay layer is typically less than about 150 grams per square meter (gsm), and in some embodiments, between about 10 gsm to about 100 gsm. If desired, the transfer delay layer may contain the nonwoven web (e.g., spunbond web) of the present invention.

The absorbent member may also include a composite absorbent layer, such as a coform material. In this instance, fluids may be wicked from the transfer delay layer into the composite absorbent member. The composite absorbent layer may be formed separately from the surge layer and/or transfer delay layer, or may be formed simultaneously therewith. In one embodiment, for example, the composite absorbent layer may be formed on the transfer delay layer or surge layer, which acts a carrier during the coform process described above.

Besides the above-mentioned components, the absorbent article 201 may also contain various other components as is known in the art. For example, the absorbent article 201 may also contain a substantially hydrophilic wrapsheet (not illustrated) that helps maintain the integrity of the fibrous structure of the absorbent core layer 203. The wrapsheet is typically placed about the absorbent core layer 203 over at least the two major facing surfaces thereof, and composed of an absorbent cellulosic material, such as creped wadding or a high wet-strength tissue. The wrapsheet may be configured to provide a wicking layer that helps to rapidly distribute liquid over the mass of absorbent fibers of the absorbent core layer 203. The wrapsheet material on one side of the absorbent fibrous mass may be bonded to the wrapsheet located on the opposite side of the fibrous mass to effectively entrap the absorbent core layer 203. Furthermore, the absorbent article 201 may also include a ventilation layer (not shown) that is positioned between the absorbent core layer 203 and the backsheet 217. When utilized, the ventilation layer may help insulate the backsheet 217 from the absorbent core layer 203, thereby reducing dampness in the backsheet 217. Examples of such ventilation layers may include a nonwoven web laminated to a breathable film, such as described in U.S. Pat. No. 6,663,611 to Blaney, et al. If desired, the wrapsheet and/or ventilation layer may contain the nonwoven web of the present invention.

In some embodiments, the absorbent article 201 may also include a pair of ears (not shown) that extend from the side edges 232 of the absorbent article 201 into one of the waist regions. The ears may be integrally formed with a selected diaper component. For example, the ears may be integrally formed with the backsheet 217 or from the material employed to provide the top surface, which may include the nonwoven web of the present invention if so desired. In alternative configurations, the ears may be provided by members connected and assembled to the backsheet 217, the top surface, between the backsheet 217 and top surface, or in various other configurations. As noted above, the ears may contain the nonwoven web of the present invention if so desired.

As representatively illustrated in FIG. 1, the absorbent article 201 may also include a pair of containment flaps 212 that are configured to provide a barrier and to contain the lateral flow of body exudates. The containment flaps 212 may be located along the laterally opposed side edges 232 of the topsheet 205 adjacent the side edges of the absorbent core layer 203. The containment flaps 212 may extend longitudinally along the entire length of the absorbent core layer 203, or may only extend partially along the length of the absorbent core layer 203. When the containment flaps 212 are shorter in length than the absorbent core layer 203, they may be selectively positioned anywhere along the side edges 232 of absorbent article 201 in a crotch region 210. In one embodiment, the containment flaps 212 extend along the entire length of the absorbent core layer 203 to better contain the body exudates. Such containment flaps 212 are generally well known to those skilled in the art. For example, suitable constructions and arrangements for the containment flaps 212 are described in U.S. Pat. No. 4,704,116 to Enloe. If desired, the containment flaps may contain the nonwoven web of the present invention.

The absorbent article 201 may include various elastic or stretchable materials, such as a pair of leg elastic members 206 affixed to the side edges 232 to further prevent leakage of body exudates and to support the absorbent core layer 203. In addition, a pair of waist elastic members 208 may be affixed to longitudinally opposed waist edges 215 of the absorbent article 201. The leg elastic members 206 and the waist elastic members 208 are generally adapted to closely fit about the legs and waist of the wearer in use to maintain a positive, contacting relationship with the wearer and to effectively reduce or eliminate the leakage of body exudates from the absorbent article 201. The absorbent article 201 may also include one or more fasteners 230. For example, two flexible fasteners 130 are illustrated in FIG. 1 on opposite side edges of waist regions to create a waist opening and a pair of leg openings about the wearer. The shape of the fasteners 230 may generally vary, but may include, for instance, generally rectangular shapes, square shapes, circular shapes, triangular shapes, oval shapes, linear shapes, and so forth. The fasteners may include, for instance, a hook material. In one particular embodiment, each fastener 230 includes a separate piece of hook material affixed to the inside surface of a flexible backing. The elastic members (e.g., leg, waist, etc.) and/or fasteners may contain the nonwoven web of the present invention if desired.

The various regions and/or components of the absorbent article 201 may be assembled together using any known attachment mechanism, such as adhesive, ultrasonic, thermal bonds, etc. Suitable adhesives may include, for instance, hot melt adhesives, pressure-sensitive adhesives, and so forth. When utilized, the adhesive may be applied as a uniform layer, a patterned layer, a sprayed pattern, or any of separate lines, swirls or dots. In the illustrated embodiment, for example, the backsheet 217 and topsheet 205 are assembled to each other and to the absorbent core layer 203 using an adhesive. Alternatively, the absorbent core layer 203 may be connected to the backsheet 217 using conventional fasteners, such as buttons, hook and loop type fasteners, adhesive tape fasteners, and so forth. Similarly, other diaper components, such as the leg elastic members 206, waist elastic members 208 and fasteners 230, may also be assembled into the absorbent article 201 using any attachment mechanism.

Although various configurations of a diaper have been described above, it should be understood that other diaper and absorbent article configurations are also included within the scope of the present invention. In addition, the present invention is by no means limited to diapers. In fact, any other absorbent article may be formed in accordance with the present invention, including, but not limited to, other personal care absorbent articles, such as training pants, absorbent underpants, adult incontinence products, feminine hygiene products (e.g., sanitary napkins), swim wear, baby wipes, and so forth; medical absorbent articles, such as garments, fenestration materials, underpads, bandages, absorbent drapes, and medical wipes; food service wipers; clothing articles; and so forth.

The present invention may be better understood with reference to the following examples.

Test Methods

Melt Flow Rate:

The melt flow rate ("MFR") is the weight of a polymer (in grams) forced through an extrusion rheometer orifice (0.0825-inch diameter) when subjected to a load of 2160 grams in 10 minutes, typically at 190° C., 210° C., or 230° C. Unless otherwise indicated, melt flow rate is measured in accordance with ASTM Test Method D1238 with a Tinius Olsen Extrusion Plastometer.

Thermal Properties:

The glass transition temperature ($T_g$) may be determined by dynamic mechanical analysis (DMA) in accordance with ASTM E1640-09. A Q800 instrument from TA Instruments may be used. The experimental runs may be executed in tension/tension geometry, in a temperature sweep mode in the range from −120° C. to 150° C. with a heating rate of 3° C./min. The strain amplitude frequency may be kept constant (2 Hz) during the test. Three (3) independent samples may be tested to get an average glass transition temperature, which is defined by the peak value of the tan δ curve, wherein tan δ is defined as the ratio of the loss modulus to the storage modulus (tan δ=E"/E').

The melting temperature may be determined by differential scanning calorimetry (DSC). The differential scanning calorimeter may be a DSC Q100 Differential Scanning Calorimeter, which was outfitted with a liquid nitrogen cooling accessory and with a UNIVERSAL ANALYSIS 2000 (version 4.6.6) analysis software program, both of which are available from T.A. Instruments Inc. of New Castle, Del. To avoid directly handling the samples, tweezers or other tools are used. The samples are placed into an aluminum pan and weighed to an accuracy of 0.01 milligram on an analytical balance. A lid is crimped over the material sample onto the pan. Typically, the resin pellets are placed directly in the weighing pan.

The differential scanning calorimeter is calibrated using an indium metal standard and a baseline correction is performed, as described in the operating manual for the differential scanning calorimeter. A material sample is placed into the test chamber of the differential scanning calorimeter for testing, and an empty pan is used as a reference. All testing is run with a 55-cubic centimeter per minute nitrogen (industrial grade) purge on the test chamber. For resin pellet samples, the heating and cooling program is a 2-cycle test that began with an equilibration of the chamber to −30° C., followed by a first heating period at a heating rate of 10° C. per minute to a temperature of 200° C., followed by equilibration of the sample at 200° C. for 3 minutes, followed by a first cooling period at a cooling rate of 10° C. per minute to a temperature of −30° C., followed by equilibration of the sample at −30° C. for 3 minutes, and then a second heating period at a heating rate of 10° C. per minute to a temperature of 200° C. All testing is run with a 55-cubic centimeter per minute nitrogen (industrial grade) purge on the test chamber.

The results are evaluated using the UNIVERSAL ANALYSIS 2000 analysis software program, which identified and quantified the glass transition temperature ($T_g$) of inflection, the endothermic and exothermic peaks, and the areas under the peaks on the DSC plots. The glass transition temperature is identified as the region on the plot-line where a distinct change in slope occurred, and the melting temperature is determined using an automatic inflection calculation.

Tensile Properties:

The tensile properties may be determined in accordance with ASTM 638-10 at 23° C. For instance, individual fiber specimens may initially be shortened (e.g., cut with scissors) to 38 millimeters in length, and placed separately on a black velvet cloth. 10 to 15 fiber specimens may be collected in this manner. The fiber specimens may then be mounted in a substantially straight condition on a rectangular paper frame having external dimension of 51 millimeters×51 millimeters and internal dimension of 25 millimeters×25 millimeters. The ends of each fiber specimen may be operatively attached to the frame by carefully securing the fiber ends to the sides of the frame with adhesive tape. Each fiber specimen may be measured for its external, relatively shorter, cross-fiber dimension employing a conventional laboratory microscope, which may be properly calibrated and set at 40× magnification. This cross-fiber dimension may be recorded as the diameter of the individual fiber specimen. The frame helps to mount the ends of the sample fiber specimens in the upper and lower grips of a constant rate of extension type tensile tester in a manner that avoids excessive damage to the fiber specimens.

A constant rate of extension type of tensile tester and an appropriate load cell may be employed for the testing. The load cell may be chosen (e.g., 10N) so that the test value falls within 10-90% of the full scale load. The tensile tester (i.e., MTS SYNERGY 200) and load cell may be obtained from MTS Systems Corporation of Eden Prairie, Mich. The fiber specimens in the frame assembly may then be mounted between the grips of the tensile tester such that the ends of the fibers may be operatively held by the grips of the tensile tester. Then, the sides of the paper frame that extend parallel to the fiber length may be cut or otherwise separated so that the tensile tester applies the test force only to the fibers. The fibers may be subjected to a pull test at a pull rate and grip speed of 12 inches per minute. The resulting data may be analyzed using a TESTWORKS 4 software program from the MTS Corporation with the following test settings:

| Calculation Inputs | | Test Inputs | |
|---|---|---|---|
| Break mark drop | 50% | Break sensitivity | 90% |
| Break marker elongation | 0.1 in | BreaK threshold | 10 $g_f$ |
| Nominal gage length | 1 in | Data Acq. Rate | 10 Hz |
| Slack pre-load | 1 $lb_f$ | Denier length | 9000 m |
| Slope segment length | 20% | Density | 1.25 g/cm$^3$ |
| Yield offset | 0.20% | Initial speed | 12 in/min |
| Yield segment length | 2% | Secondary speed | 2 in/min |

The tenacity values may be expressed in terms of gram-force per denier Peak elongation (% strain at break) and, peak stress may also be measured.

The peak load of a web may be determined using a 2"×6" strip cut along the length (MD) and width direction (CD). The test may be performed in a universal tensile tester equipped with two 1"×3" rubber coated grips. The gauge length may be 76±1 mm (3±0.04").

Density and Percent Void Volume:

To determine density and percent void volume, the width ($W_i$) and thickness ($T_i$) of the specimen may be initially measured prior to drawing. The length ($L_i$) before drawing may also be determined by measuring the distance between two markings on a surface of the specimen. Thereafter, the specimen may be drawn to initiate pore formation. The width ($W_f$), thickness ($T_f$), and length ($L_f$) of the specimen may then be measured to the nearest 0.01 mm utilizing Digimatic Caliper (Mitutoyo Corporation). The volume ($V_i$) before drawing may be calculated by $W_i \times T_i \times L_i = V_i$. The volume ($V_f$) after drawing may also be calculated by $W_f \times T_f \times L_f = V_f$. The density ($P_f$) may be calculated by $P_f = P_i/\phi$, where $P_i$ is density of precursor material, and the percent void volume (% $V_v$) was calculated by: % $V_v = (1 - 1/\phi) \times 100$.

Hydrostatic Pressure Test ("Hydrohead"):

The hydrostatic pressure test is a measure of the resistance of a material to penetration by liquid water under a static pressure and is performed in accordance with AATCC Test Method 127-2008. The results for each specimen may be averaged and recorded in centimeters (cm). A higher value indicates greater resistance to water penetration.

Water Vapor Transmission Rate ("WVTR"):

The test used to determine the WVTR of a material may vary based on the nature of the material. One technique for measuring the WVTR value is ASTM E96/96M-12, Procedure B. Another method involves the use of INDA Test Procedure IST-70.4 (01). The INDA test procedure is summarized as follows. A dry chamber is separated from a wet chamber of known temperature and humidity by a permanent guard film and the sample material to be tested. The purpose of the guard film is to define a definite air gap and to quiet or still the air in the air gap while the air gap is characterized. The dry chamber, guard film, and the wet chamber make up a diffusion cell in which the test film is sealed. The sample holder is known as the Permatran-W Model 100K manufactured by Mocon/Modem Controls, Inc., Minneapolis, Minn. A first test is made of the WVTR of the guard film and the air gap between an evaporator assembly that generates 100% relative humidity. Water vapor diffuses through the air gap and the guard film and then mixes with a dry gas flow that is proportional to water vapor concentration. The electrical signal is routed to a computer for processing. The computer calculates the transmission rate of the air gap and the guard film and stores the value for further use.

The transmission rate of the guard film and air gap is stored in the computer as CalC. The sample material is then sealed in the test cell. Again, water vapor diffuses through the air gap to the guard film and the test material and then mixes with a dry gas flow that sweeps the test material. Also, again, this mixture is carried to the vapor sensor. The computer then calculates the transmission rate of the combination of the air gap, the guard film, and the test material. This information is then used to calculate the transmission rate at which moisture is transmitted through the test material according to the equation:

$$TR^{-1}_{test\ material} = TR^{-1}_{test\ material, guardfilm, airgap} - TR^{-1}_{guardfilm,\ airgap}$$

The water vapor transmission rate ("WVTR") is then calculated as follows:

$$WVTR = \frac{F \rho_{sat(T)} RH}{A P_{sat(T)}(1-RH)}$$

wherein,

F=the flow of water vapor in cm$^3$ per minute;

$\rho_{sat(T)}$=the density of water in saturated air at temperature T;

RH=the relative humidity at specified locations in the cell;

A=the cross sectional area of the cell; and $P_{sat(T)}$=the saturation vapor pressure of water vapor at temperature T.

Frazier Porosity:

The Frazier porosity was measured in a Frazier® Low Differential Pressure Air Permeability Tester (FAP-LP) by cutting an 8" strip (measured along the machine direction) of a sample and folding the sample accordion style (in the direction) to obtain six layers.

Example 1

A precursor blend was formed from 91.8 wt. % isotactic propylene homopolymer (M3661, melt flow rate of 14 g/10 at 210° C. and melting temperature of 150° C., Total Petrochemicals), 7.4 wt. % polylactic acid (PLA 6252, melt flow rate of 70 to 85 g/10 min at 210° C., Natureworks®) and 0.7 wt. % of a polyepoxide. The polyepoxide was poly(ethylene-co-methyl acrylate-co-glycidyl methacrylate) (LOTADER® AX8900, Arkema) having a melt flow rate of 6 g/10 min (190° C./2160 g), a glycidyl methacrylate content of 8 wt. %, methyl acrylate content of 24 wt. %, and ethylene content of 68 wt. %. The components were compounded in a co-rotating twin-screw extruder (Werner and Pfleiderer ZSK-30 with a diameter of 30 mm and a L/D=44). The extruder had seven heating zones. The temperature in the extruder ranged from 180° C. to 220° C. The polymer was fed gravimetrically to the extruder at the hoper at 15 pounds per hour and the liquid was injected into the barrel using a peristaltic pump. The extruder was operated at 200 revolutions per minute (RPM). In the last section of the barrel (front), a 3-hole die of 6 mm in diameter was used to form the extrudate. The extrudate was air-cooled in a conveyor belt and pelletized using a Conair Pelletizer.

Figure 2:
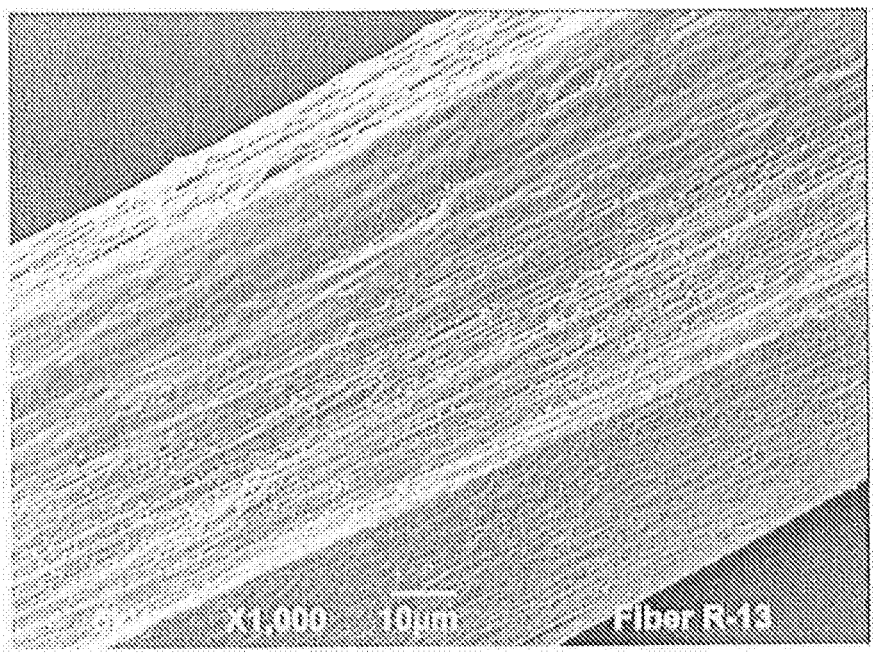
FIG. 2 is an SEM photomicrograph (1,000×) of the fiber of Example 1 (polypropylene, polylactic acid, and polyepoxide) after freeze fracturing in liquid nitrogen.
Figure 3:
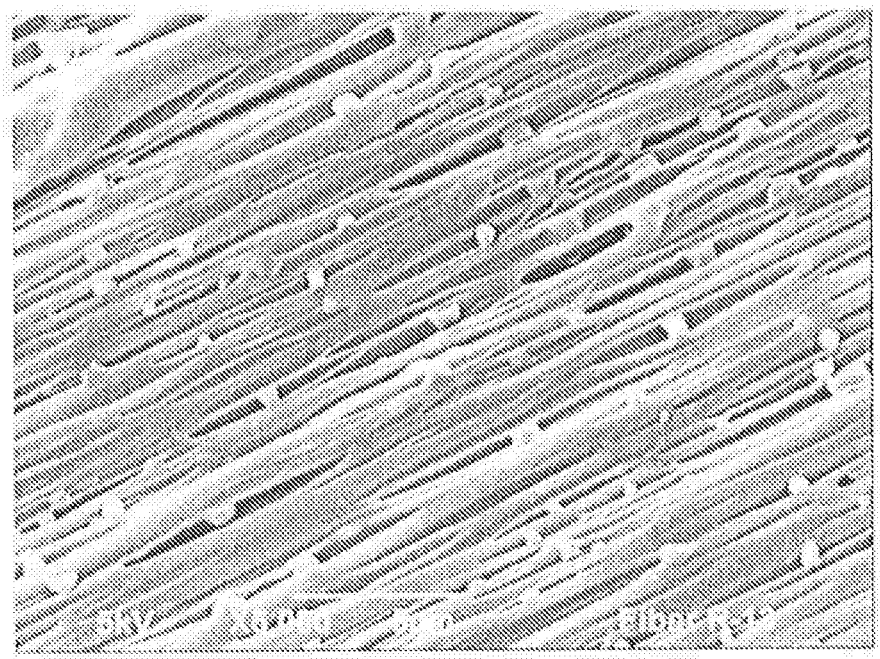
FIG. 3 is an SEM photomicrograph (5,000×) of the fiber of Example 1 (polypropylene, polylactic acid, and polyepoxide) after freeze fracturing in liquid nitrogen.
Figure 4:
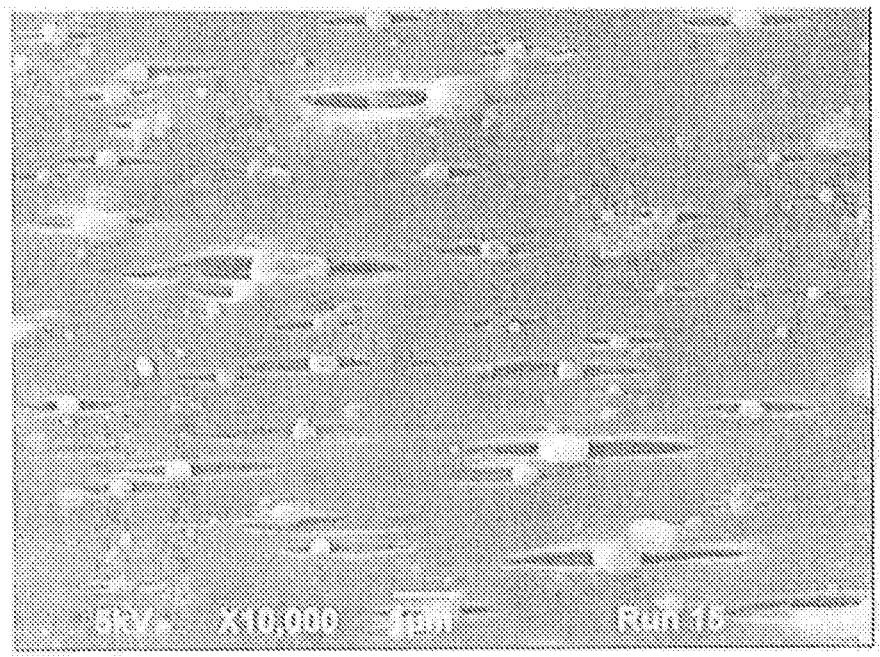
FIG. 4 is an SEM photomicrograph (10,000×) of the fiber surface of Example 1 (polypropylene, polylactic acid, and polyepoxide)

Fiber was then produced from the precursor blend using a Davis-Standard fiber spinning line equipped with a 0.75-inch single screw extruder and 16 hole spinneret with a diameter of 0.6 mm. The fibers were collected at different draw down ratios. The take up speed ranged from 1 to 1000 m/min. The temperature of the extruder ranged from 175° C. to 220° C. The fibers were stretched in a tensile tester machine at 300 mm/min up to 400% elongation at 25° C. To analyze the material morphology, the fibers were freeze fractured in liquid nitrogen and analyzed via Scanning Electron Microscope Jeol 6490LV at high vacuum. The results are shown in FIG. 2-4. As shown, spheroidal pores are formed that are highly elongated in the stretching direction. Both nanopores (~50 nanometers in width, ~500 nanometers in length) and micropores (~0.5 micrometers in width, ~4 micrometers in length) were formed.

Example 2

Figure 5:
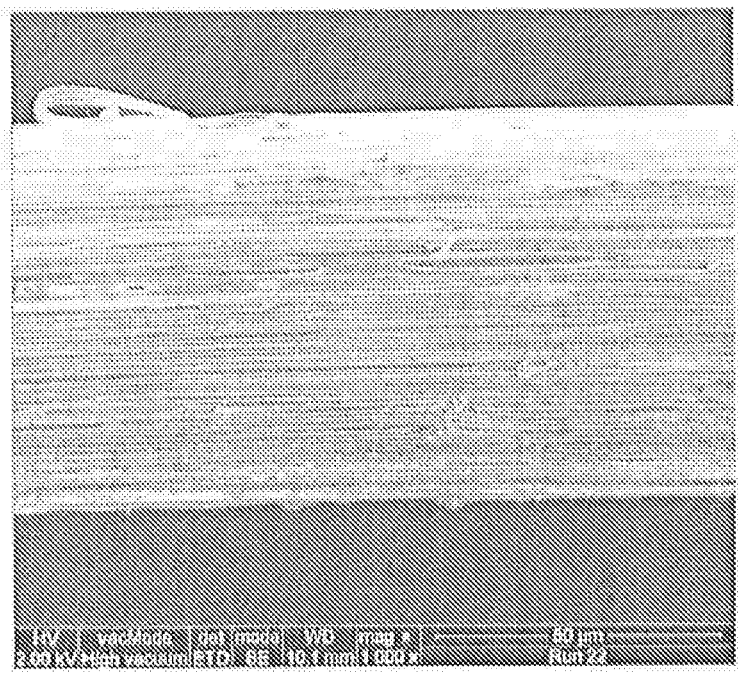
FIG. 5 is an SEM photomicrograph (1,000×) along the axial dimension of the fiber of Example 2 (polypropylene and polyepoxide) after freeze fracturing in liquid nitrogen.
Figure 6:
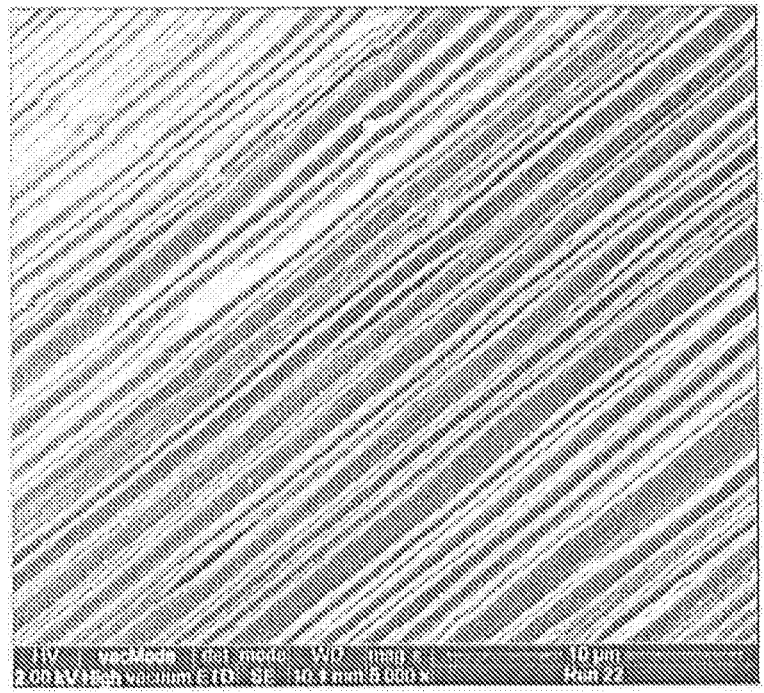
FIG. 6 is an SEM photomicrograph (5,000×) along the axial dimension of the fiber of Example 2 (polypropylene and polyepoxide) after freeze fracturing in liquid nitrogen.

A blend of 93 wt. % polypropylene (Total M3661) and 7 wt. % Lotader® AX8900) were compounded in a co-rotating twin-screw extruder (Werner and Pfleiderer ZSK-30 with a diameter of 30 mm and a L/D=44). The extruder had seven heating zones. The temperature in the extruder ranged from 180° C. to 220° C. The polymer was feed gravimetrically to the extruder at the hoper at 15 pounds per hour. The extruder was operated at 200 revolutions per minute (RPM). In the last section of the barrel (front), a 3-hole die of 6 mm in diameter was used to form the extrudate. The extrudate was air-cooled in a conveyor belt and pelletized using a Conair Pelletizer. Fiber was then produced from the precursor blend using a Davis-Standard fiber spinning line equipped with a 0.75-inch single screw extruder and 16 hole spinneret with a diameter of 0.6 mm. The fibers were collected at different draw down ratios. The take up speed ranged from 1 to 1000 m/min. The temperature of the extruder ranged from 175° C. to 220° C. The fibers were stretched in a tensile tester machine at 300 mm/min up to 400% elongation at 25° C. To analyze the material morphology, the fibers were freeze fractured in liquid nitrogen and analyzed via Scanning Electron Microscope Jeol 6490LV at high vacuum. The results are shown in FIG. 5-6.

Example 3

Figure 7:
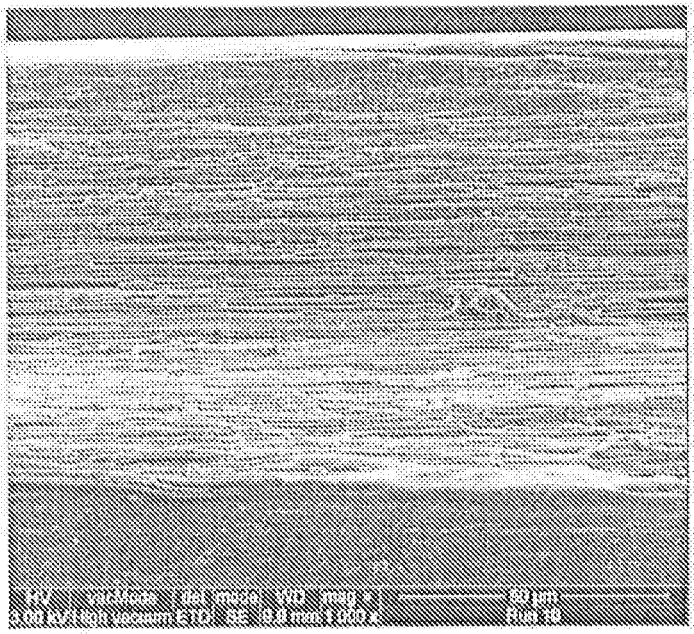
FIG. 7 is an SEM photomicrograph (1,000×) along the axial dimension of the fiber of Example 3 (polypropylene, polylactic acid, polyepoxide, and interphase modifier) after freeze fracturing in liquid nitrogen.
Figure 8:
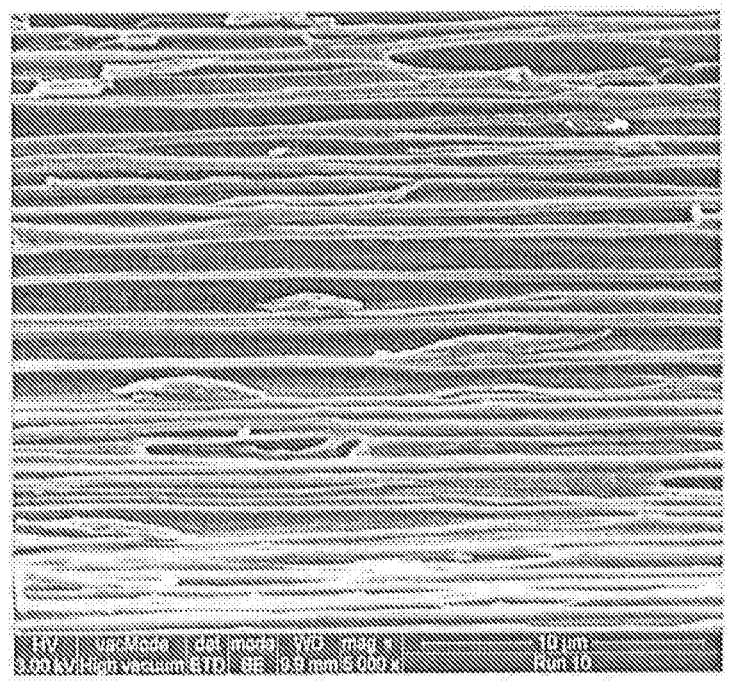
FIG. 8 is an SEM photomicrograph (5,000×) along the axial dimension of the fiber of Example 2 (polypropylene, polylactic acid, polyepoxide, and interphase modifier) after freeze fracturing in liquid nitrogen.
Figure 7:
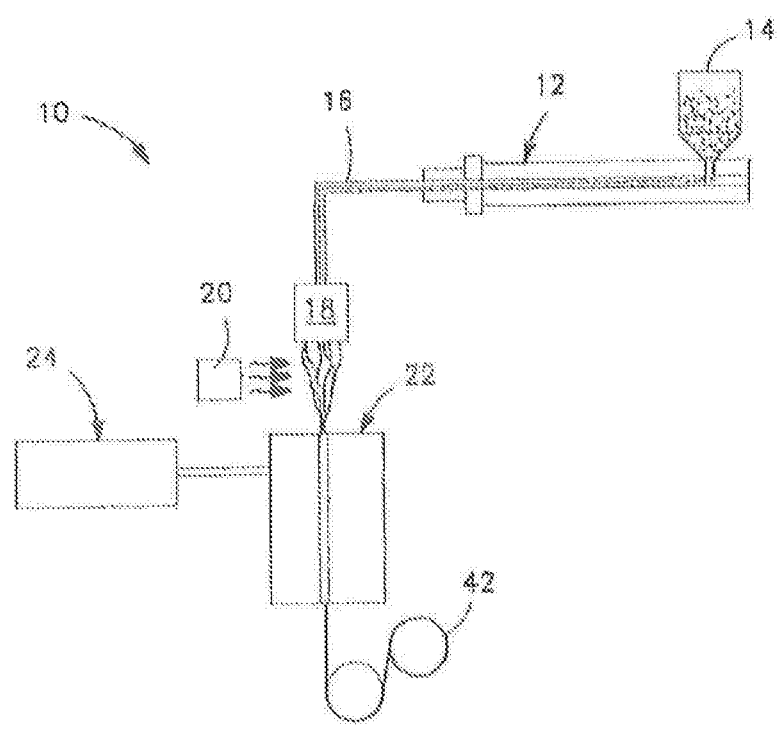

A blend of 91.1 wt. % polypropylene (Total M3661), 7.4 wt. % polylactic acid (NatureWorks 6251), and 1.5% Lotader® AX8900) were compounded in the extruder and the conditions described in Example 2. In this case, 5% of Pluriol® WI 285 was then injected to the barrel using a peristaltic pump. Fiber was then produced from the precursor blend using a Davis-Standard fiber spinning line equipped with a 0.75-inch single screw extruder and 16 hole spinneret with a diameter of 0.6 mm. The fibers were collected at different draw down ratios. The take up speed ranged from 1 to 1000 m/min. The temperature of the extruder ranged from 175° C. to 220° C. The fibers were stretched in a tensile tester machine at 300 mm/min up to 400% elongation at 25° C. To analyze the material morphology, the fibers were freeze fractured in liquid nitrogen and analyzed via Scanning Electron Microscope Jeol 6490LV at high vacuum. The results are shown in FIG. 7-8.

Example 4

A precursor polymer blend was made that contained 91.8 wt % of isotactic polypropylene (M3661, melt flow rate of 14 g/10 min at 230° C. and melting temperature of 150° C., Total Petrochemicals), 7.45% polylactic acid (PLA) (Ingeo 6251D, melt flow rate 70-85 g/10 at 210° C., Natureworks), and 0.75% polyepoxide compatibilizer (Arkema Lotader® AX8900). The polyepoxide modifier was poly(ethylene-co-methyl acrylate-co-glycidyl methacrylate) (Lotader® AX8900, Arkema) having a melt flow rate of 5-6 g/10 min (190° C./2160 g), a glycidyl methacrylate content of 7 to 11 wt. %, methyl acrylate content of 13 to 17 wt. %, and ethylene content of 72 to 80 wt. %. The components were compounded in a co-rotating twin screw extruder (Werner and Pfleiderer ZSK-30 with a diameter of 30 mm and a L/D=44). The extruder had seven heating zones. The temperature in the extruder ranged from 180° C. to 220° C. The polymer was fed gravimetrically to the extruder at the hoper at 6.8 Kilograms per hour (15 pounds per hour). The extruder was operated at 200 revolutions per minute (RPM). In the last section of the barrel (front), a 3-hole die of 6 mm in diameter was used to form the extrudate. The extrudate was air-cooled in a conveyor belt and pelletized using a Conair Pelletizer.

Example 5

Figure 10:
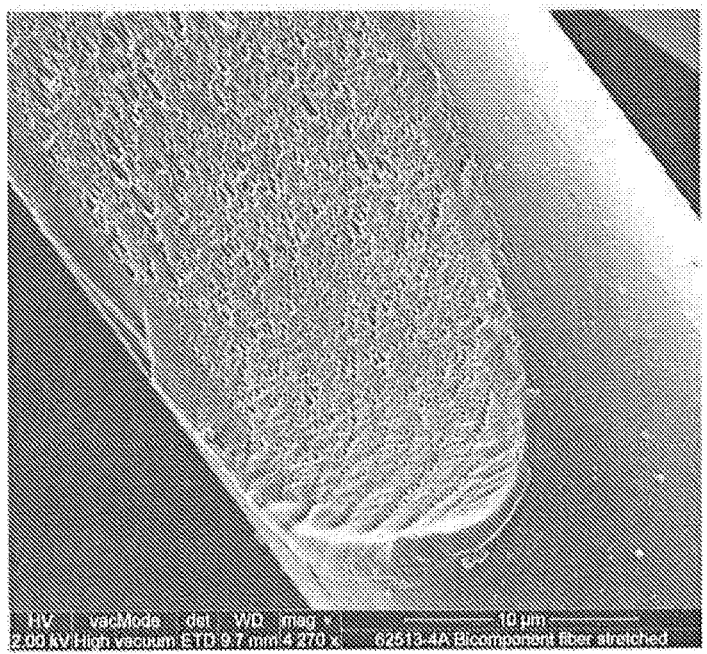
FIG. 10 is an SEM photomicrograph (4,270×) of the fiber of Example 5 after freeze fracturing in liquid nitrogen.
Figure 11:
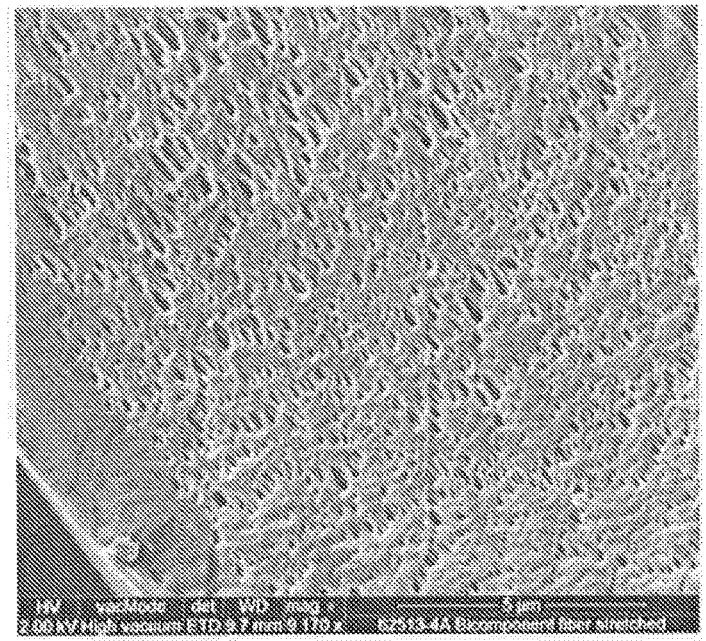
FIG. 11 is an SEM photomicrograph (9,170×) of the fiber of Example 5 after freeze fracturing in liquid nitrogen.

Bicomponent fibers were produced in a bicomponent fiber line equipped with 2 single screw extruders (1.25-in diameter). The bicomponent fiber had a 30/70, sheath/core configuration, in which the sheath was formed from 100 wt. % polypropylene (M3661, Total Petrochemicals) and the core was formed from the blend of Example 4. The extruders fed the sheath and core polymer compositions into one spinneret of 288 capillaries of 0.5 mm in diameter and 4:1 length/diameter ratio (L/D). The fibers were spun at a rate of 8 kg/hr at a spinning velocity of 660 meters per minute and collected in spools for post-stretching process. The extrusion temperature profile for both sheath and core was as follows Zone 1=220° C., Zone 2=225° C., Zone 3=230° C., Zone 4=240° C., and Spin Beam=240° C. The melt spun fibers were then stretched at room temperature (25° C.) to 200% between two godet rolls (single step draw) at a rate of 1200 meters per minute. Then, the fibers were crimped (19 crimps per inch) and cut to a length of 38 mm. The fibers were then cut with a razor blade in liquid nitrogen and analyzed via scanning electron microscopy. The fractured surfaced were sputter-coated with gold-palladium in a Denton Vacuum Desk V sputtering system using 15 mA for 75 s and analyzed via SEM in a Field Emission Quanta 650. The results are set forth in FIGS. 10-11.

Various properties of the fibers were also tested as provided in the table below.

| Diameter (μm) | 19.4 |
| Tenacity (g/den) | 5.5 |
| Peak Stress (MPa) | 443.9 |
| Strain at Break (%) | 85.28 |
| Energy per volume at break (J/cm³) | 269.4 |

A 100-gsm, through-air bonded carded web (TABCW) was also formed with a blend of the fibers of Example 5 (70 wt. %) and bicomponent sheath/core PE/PP fibers (30 wt. %). The web was formed in a Truetzschler High-Speed Card EWK 413 equipped with a Asselin Profile 415-FD crosslapper and a Fleissner Oven (NC State University). The carded web was through air bonded at 260° F. and the final thickness was 5.5 mm.

Example 6

Figure 12:
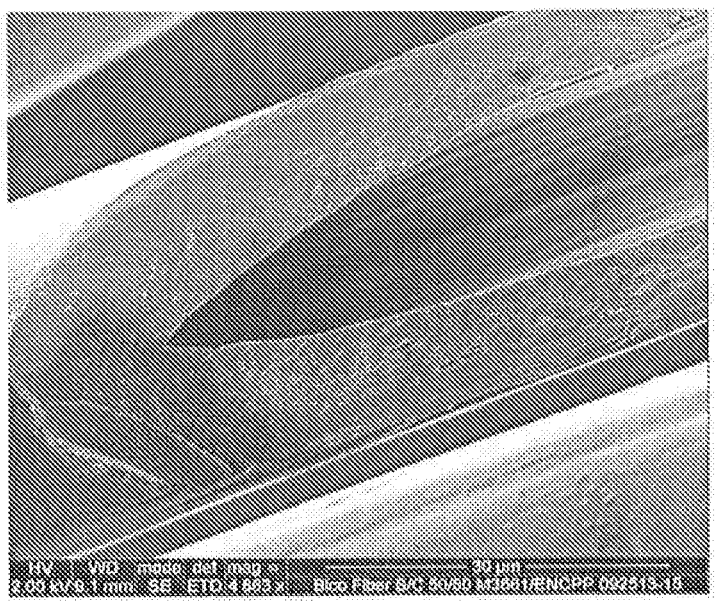
FIGS. 12-13 are SEM photomicrographs of the fiber of Example 6 after freeze fracturing in liquid nitrogen.
Figure 13:
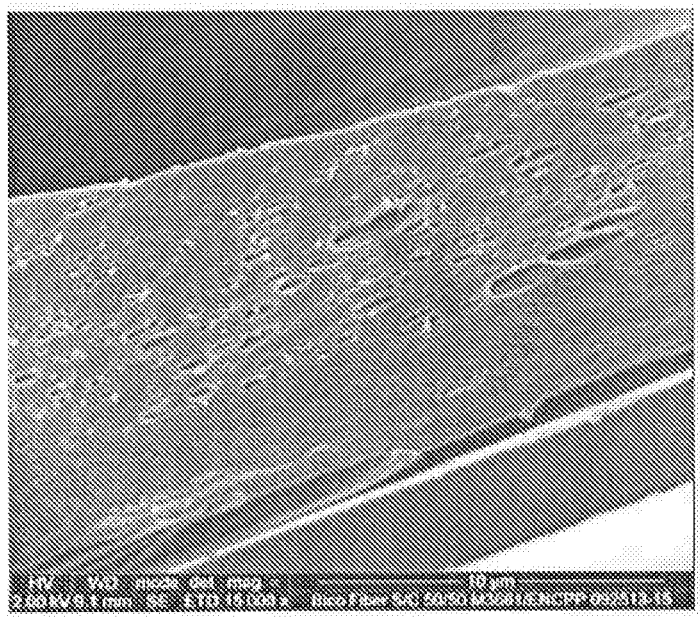

A precursor polymer blend was made as described in Example 4 that contained 93 wt % polypropylene matrix (M3661, Total Petrochemicals) and 7 wt. % of Lotader® AX8900. Ho low bicomponent fibers were produced in a bicomponent fiber line equipped with 2 single screw extruders (1.25-in diameter). The bicomponent fiber had a 50/50, sheath/core configuration, in which the sheath formed from 100 wt. % polypropylene (Achieve 3854) and the core was formed from the blend described above. The extruders fed the sheath and core polymer compositions into one spinneret of 72 capillaries of 4C-segments capillary design. The fibers were spun at a rate of 2 kg/hr at a spinning velocity of 198 meters per minute and collected in spools for post-stretching process. The extrusion temperature profile for, both sheath and core was as follows: Zone 1=220° C., Zone 2=225° C., Zone 3=230° C. Zone 4=240° C., and Spin Beam=240° C. The fiber was quenched in a water bath located 35 cm below the spinneret. The quenched fibers were then stretched at room temperature (25° C.) to 200% between two godet rolls (single step draw) at a rate of 1200 meters per minute. The fibers were then cut with a razor blade in liquid nitrogen and analyzed via scanning electron microscopy. The fractured surfaced were sputter-coated with gold-palladium in a Denton Vacuum Desk V sputtering system using 15 mA for 75 s and analyzed via SEM in a Field Emission Quanta 650. The results are set forth in FIGS. 12-13. Various properties of the fibers were also tested as provided in the table below.

| Diameter (μm) | 31.4 |
| Tenacity (g/den) | 3.8 |
| Peak Stress (MPa) | 303.8 |
| Strain at Break (%) | 90.0 |
| Energy per volume at break (J/cm³) | 223.1 |

Example 7

A precursor blend was formed as described in Example 4, except that the material was produced using a 64 mm co-rotating twin screw extruder at a production rate of 270 kilograms per hour (600 pounds per hour) and temperature of 220° C. The molten polymer blend was extruded through a multi-filament die, quenched via water and cut in to a pellet via underwater pelletizing system such as those available from Gala Industries of Eagle Rock, Va. A monocomponent fiber was formed from the blend at a rate of 22.5 kilograms per hour in a monocomponent fiber spinning line (FiberVisions) equipped with a 1.25 single screw extruder 24 L/D and two spinnerets, each one having 675 round capillaries (1,350 total) of 0.35 mm in diameter and 4:1 L/D ratio. The spinning speed was 435 meters per minute. The 7 extruder heating zones and the spin beam temperature profile were kept at 220° C. The spinning line was equipped with a single-sided air flow quench box and the air temperature was 21° C. The melt drawn fibers were collected in 5 pound spools with no cold drawing. The melt oriented fibers had a denier of 10.7 denier per filament.

Figure 14:
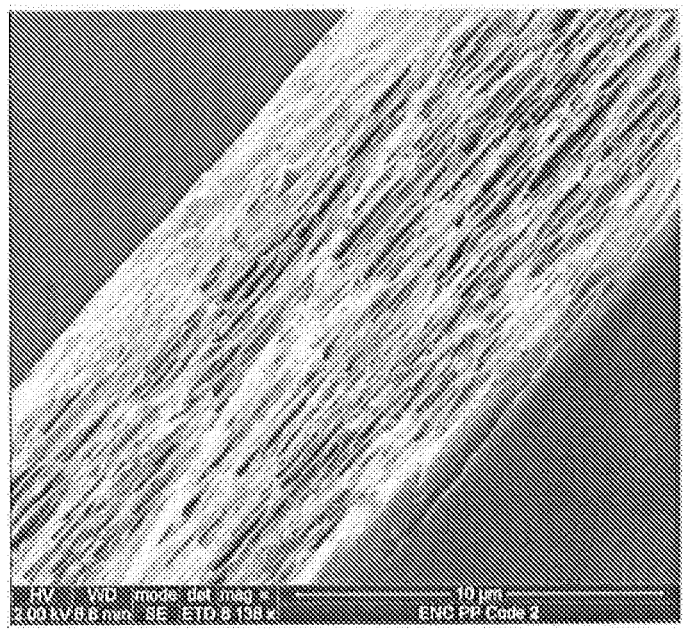
FIG. 14 is an SEM photomicrograph of the fiber of Example 7 after freeze fracturing in liquid nitrogen.

The fibers were stretched to 100% at a speed of 50 meters per minute in a stretching unit consisting of a three banks of five rolls (quintets). The temperature of the first quintet was maintained at 50° C. and the second and third quintets were maintained at a temperature of 25° C. Fibers were crimped and cut to 1.5 inches. The spin finish was adjusted before the cutting unit to 0.5%. The fibers were then cut with a razor blade in liquid nitrogen and analyzed via scanning electron microscopy. The fractured surfaced were sputter-coated with gold-palladium in a Denton Vacuum Desk V sputtering system using 15 mA for 75 s and analyzed via SEM in a Field Emission Quanta 650. The results are set forth in FIG. 14. Various properties of the fibers were also tested as provided in the table below.

| Diameter (μm) | 29.6 |
|---|---|
| Tenacity (g/den) | 3.1 |
| Peak Stress (MPa) | 244.3 |
| Strain at Break (%) | 298.8 |
| Energy per volume at break (J/cm$^3$) | 433.0 |

Figure 15:
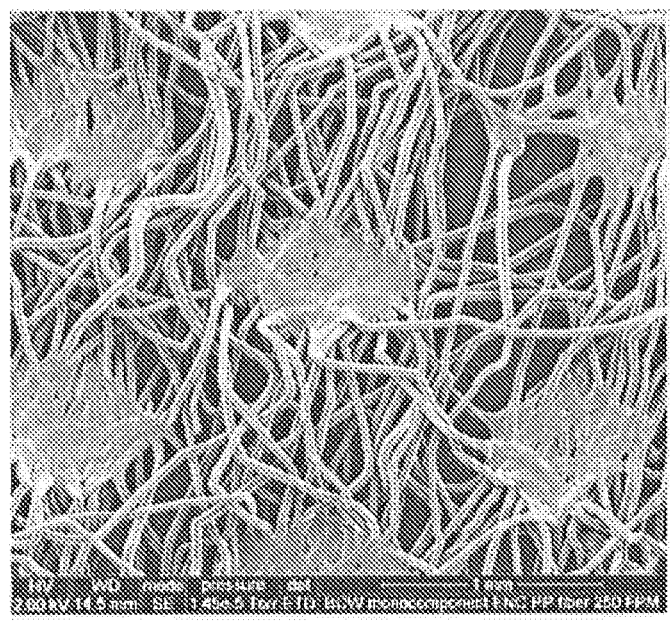
FIG. 15 is an SEM photomicrographs of the bonded web of Example 7.

Thermally bonded carded webs (30 gsm) were also produced on a carding line. To thermally bond the webs, diamond bonding pattern was used as shown in FIG. 15. The calendar temperature was 150° C. and the carding speed was 250 feet per minute. Various properties of the web were then tested as provided below.

| Basis weight (gsm) | 30 |
|---|---|
| Peak Load Machine Direction (lb$_f$) | 6.46 |
| Peak Load Transversal direction (lb$_f$) | 1.2 |
| Frazier Test 6 Layers (ft$^3$/min) | 298 |

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. An absorbent article that contains an absorbent member positioned between a backsheet and topsheet, wherein the absorbent article comprises a nonwoven web that includes a plurality of fibers formed from a thermoplastic composition that contains a continuous phase that includes a polyolefin matrix polymer and a polymeric nanoinclusion additive and a polymeric microinclusion additive dispersed within the continuous phase in the form of discrete domains,
   wherein the polymeric nanoinclusion additive is in the form of nano-scale domains and the polymeric microinclusion additive is in the form of micro-scale domains,
   wherein a porous network is defined in the composition that includes a plurality of nanopores adjacent to the nano-scale domains and/or the micro-scale domains, the nanopores having an average cross-sectional dimension of about 800 nanometers or less.

2. The absorbent article of claim 1, wherein the nanopores have an average cross-sectional dimension of from about 5 to about 700 nanometers.

3. The absorbent article of claim 1, wherein the nanopores have an average axial dimension of from about 100 to about 5000 nanometers.

4. The absorbent article of claim 1, wherein the polyolefin matrix polymer has a melt flow rate of from about 0.5 to about 80 grams per 10 minutes, determined at a load of 2160 grams and at 230° C. in accordance with ASTM D1238.

5. The absorbent article of claim 1, wherein the polyolefin matrix polymer is a propylene homopolymer, propylene/α-olefin copolymer, ethylene/α-olefin copolymer, or a combination thereof.

6. The absorbent article of claim 1, wherein the polyolefin matrix polymer is a substantially isotactic polypropylene homopolymer or a copolymer containing at least about 90% by weight propylene.

7. The absorbent article of claim 1, wherein the continuous phase constitutes from about 60 wt. % to about 99 wt. % of the thermoplastic composition.

8. The absorbent article of claim 1, wherein the polymeric nanoinclusion additive includes a functionalized polyolefin.

9. The absorbent article of claim 8, wherein the functionalized polyolefin is a polyepoxide.

10. The absorbent article of claim 1, wherein the polymeric nanoinclusion additive has melt flow rate of from about 0.1 to about 100 grams per 10 minutes determined at a load of 2160 grams and at a temperature at least about 40° C. above the melting temperature in accordance with ASTM D1238.

11. The absorbent article of claim 1, wherein the ratio of the melt flow rate of the polyolefin matrix polymer to the melt flow rate of the polymeric nanoinclusion additive is from about 0.2 to about 8.

12. The absorbent article of claim 1, wherein the nanoscale domains have an average cross-sectional dimension of from about 1 nanometer to about 1000 nanometers.

13. The absorbent article of claim 1, wherein the polymeric nanoinclusion additive constitutes from about 0.05 wt. % to about 20 wt. % of the composition, based on the weight of the continuous phase.

14. The absorbent article of claim 1, wherein the polymeric microinclusion additive includes a styrenic copolymer, fluoropolymer, polyvinyl alcohol, polyvinyl acetate, or polyester.

15. The absorbent article of claim 14, wherein the polymeric microinclusion additive is polylactic acid.

16. The absorbent article of claim 1, wherein the microscale domains have an average axial dimension of from about 1 micrometer to about 400 micrometers.

17. The absorbent article of claim 1, wherein the polymeric microinclusion additive constitutes from about 1 wt. % to about 30 wt. % of the composition, based on the weight of the continuous phase.

18. The absorbent article of claim 1, wherein the thermoplastic composition further comprises an interphase modifier.

19. The absorbent article of claim 1, wherein the porous network further includes micropores.

20. The absorbent article of claim 1, wherein the total pore volume of the fibers is from about 15% to about 80% per cubic centimeter.

21. The absorbent article of claim 1, wherein nanopores constitute about 20 vol. % or more of the total pore volume of the polyolefin fiber.

22. The absorbent article of claim 1, wherein the thermoplastic composition has a density of about 0.90 g/cm$^3$ or less.

23. The absorbent article of claim 1, wherein the nonwoven web is a spunbond web, meltblown web, bonded carded web, coform web, hydraulically entangled web, or a combination thereof.

24. The absorbent article of claim 1, wherein the backsheet contains the nonwoven web.

25. The absorbent article of claim 1, wherein the topsheet contains the nonwoven web.

26. The absorbent article of claim 1, wherein the absorbent member contains the nonwoven web.

27. The absorbent article of claim 26, wherein the absorbent member comprises a core layer, surge layer, transfer delay layer, wrapsheet, ventilation layer, or a combination thereof, and wherein one or more of the layers contains the nonwoven web.

28. The absorbent article of claim 26, wherein the absorbent member comprises a core layer and a surge layer positioned between the core layer and the topsheet, wherein the surge layer contains the nonwoven web.

29. The absorbent article of claim 1, wherein the article contains an additional component that includes the nonwoven web, the additional component including ears, containment flaps, side panels, elastic members, fasteners, or a combination thereof.

\* \* \* \* \*